United States Patent
Guerin et al.

(10) Patent No.: US 8,597,373 B2
(45) Date of Patent: Dec. 3, 2013

(54) HAIR DYEING PROCESS USING A COMPOSITION COMPRISING AT LEAST ONE INDOLE OR INDOLINE COMPOUND, A METAL SALT, HYDROGEN PEROXIDE AND A BASIFYING AGENT

(75) Inventors: Frédéric Guerin, Paris (FR); Gilles Genain, Paris (FR); Patrick Choisy, Montlouis sur Loire (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 13/701,827

(22) PCT Filed: Jun. 13, 2011

(86) PCT No.: PCT/EP2011/059758
§ 371 (c)(1),
(2), (4) Date: Mar. 14, 2013

(87) PCT Pub. No.: WO2011/157668
PCT Pub. Date: Dec. 22, 2011

(65) Prior Publication Data
US 2013/0174864 A1 Jul. 11, 2013

(30) Foreign Application Priority Data
Jun. 16, 2010 (FR) .................................. 10 54761

(51) Int. Cl.
*A61Q 5/10* (2006.01)
(52) U.S. Cl.
USPC ................ 8/405; 8/406; 8/435; 8/570; 8/574; 8/628; 8/629; 8/646; 132/202; 132/208
(58) Field of Classification Search
USPC ............. 8/405, 406, 435, 570, 574, 628, 629, 8/646; 132/202, 208
See application file for complete search history.

(56) References Cited

U.S. PATENT DOCUMENTS

| | | | |
|---|---|---|---|
| 3,376,110 A | 4/1968 | Shiraeff et al. | |
| 4,823,985 A | 4/1989 | Grollier et al. | |
| 5,008,093 A | 4/1991 | Merianos | |
| 5,183,901 A | 2/1993 | Login et al. | |
| 5,690,697 A * | 11/1997 | Samain ............................ | 8/423 |
| 6,953,486 B2 | 10/2005 | Pruche | |
| 7,857,865 B2 | 12/2010 | Guerin et al. | |
| 2003/0103917 A1 | 6/2003 | Pruche | |
| 2003/0163878 A1 | 9/2003 | Pruche | |
| 2010/0150857 A1 | 6/2010 | Guerin et al. | |

FOREIGN PATENT DOCUMENTS

| | | |
|---|---|---|
| EP | 0697209 | 2/1996 |
| EP | 2196180 | 6/2010 |
| FR | 2586913 | 3/1987 |
| FR | 2814943 | 4/2002 |
| FR | 2814945 | 4/2002 |
| FR | 2814946 | 4/2002 |
| FR | 2814947 | 4/2002 |
| WO | 0230375 | 4/2002 |

OTHER PUBLICATIONS

STIC Search Report dated Jul. 25, 2013.*
International Search Report for PCT/EP2011/059758, dated Oct. 24, 2011 (2 pages).
PCT/IB/308 Form for PCT/EP2011/059758, dated Oct. 18, 2012 (1 page).
English Abstract for FR 2 814 943, (2002).
English Abstract for FR 2 814 945, (2002).
English Abstract for FR 2 814 946, (2002).

* cited by examiner

*Primary Examiner* — Eisa Elhilo
(74) *Attorney, Agent, or Firm* — O'Brien Jones PLLC.

(57) ABSTRACT

The invention relates to a process for dyeing keratin fibers, in which said fibers are treated: ■ with a composition (A) comprising i) one or more indole or indoline compounds; ii) one or more metal salts; iii) hydrogen peroxide or one or more systems that generate hydrogen peroxide; and then ■ with a composition (B) comprising iv) one or more basifying agents. The invention also relates to a hair dyeing process for obtaining better colorations, which are more uniform, chromatic and remanent and which do not impair the cosmetic properties of keratin fibers.

23 Claims, No Drawings

HAIR DYEING PROCESS USING A COMPOSITION COMPRISING AT LEAST ONE INDOLE OR INDOLINE COMPOUND, A METAL SALT, HYDROGEN PEROXIDE AND A BASIFYING AGENT

This is a national stage application of PCT/EP2011/059758, filed internationally on Jun. 13, 2011, which claims priority to French Application No. 1054761, filed Jun. 16, 2010, and U.S. Provisional Application No. 61/358,525, filed on Jun. 25, 2010.

The invention relates to a process for dyeing keratin fibers by treating said fibers with i) at least one indole or indoline derivative, ii) at least one metal salt, iii) at least hydrogen peroxide or a system for generating hydrogen peroxide, and iv) at least one basifying agent.

It is known practice to obtain "permanent" colorations with dye compositions containing oxidation dye precursors, which are generally known as oxidation bases, such as ortho- or para-phenylenediamines, ortho- or para-aminophenols and heterocyclic compounds. These oxidation bases are colorless or weakly colored compounds, which, when combined with oxidizing products, may give rise to colored compounds by a process of oxidative condensation. It is also known that the shades obtained with these oxidation bases may be varied by combining them with couplers or coloration modifiers, the latter being chosen especially from aromatic meta-diamines, meta-aminophenols, meta-diphenols and certain heterocyclic compounds such as indole compounds. This oxidation dyeing process consists in applying to the keratin fibers bases or a mixture of bases and couplers with hydrogen peroxide $H_2O_2$ or aqueous hydrogen peroxide solution, as oxidizing agent, in leaving it to diffuse, and then in rinsing the fibers. The colorations resulting therefrom are permanent, strong and resistant to external agents, especially to light, bad weather, washing, perspiration and rubbing.

However, commercial hair dyes that contain them may have drawbacks such as staining, and problems of odour, discomfort and degradation of the keratin fibers. This is particularly the case with oxidation dyeing.

In the field of dyeing, it is also known practice to dye keratin materials such as the hair or the skin using ortho-diphenols in the presence of a metal salt especially of Mn and/or Zn. In particular, patent applications FR 2 814 943, FR 2 814 945, FR 2 814 946 and FR 2 814 947 propose compositions for dyeing the skin or keratin fibers, comprising a dye precursor that contains at least one ortho-diphenol, Mn and/or Zn oxides and salts, alkaline agents of hydrogen carbonate type in a particular Mn, Zn/hydrogen carbonate ratio and optionally an enzyme. According to these documents, it is possible to obtain intense colorations while dispensing with the use of hydrogen peroxide. However, the colorations obtained are not strong enough, especially in the case of hair fibers.

It is also known practice to dye keratin fibers with indole or indoline derivatives in the presence of a metal salt, especially of Mn. Patent application EP 697 209 in particular describes a two-step dyeing process using, in a first step, an indole or indoline dye in the presence of a manganese salt, and, in a second step, a basifying agent optionally combined with an oxidizing agent. However, the results obtained via that process are not entirely satisfactory in terms of intensity of coloration, and the risks of bleaching and of attack of the keratin fibers are non-negligible.

There is consequently a real need to develop dyeing processes that can obtain powerful colorations using indoles or indolines, while at the same time limiting the bleaching of keratin fibers. In particular, there is a need to obtain colorations that are sparingly aggressive on the hair and that are simultaneously resistant to external agents (light, bad weather, shampooing) and that are remanent and homogeneous, while at the same time remaining powerful or chromatic.

This aim is achieved by the present invention, a subject of which is a process for dyeing keratin fibers, in which said fibers are treated:
  with a composition (A) comprising
    i) one or more indole or indoline compounds,
    ii) one or more metal salts,
    iii) hydrogen peroxide or one or more systems that generate hydrogen peroxide; and then
  with a composition (B) comprising
    iv) one or more basifying agents.

Another subject of the invention relates to a multi-compartment device comprising the ingredients i) to iv) as defined previously.

The process according to the invention has the advantage of dyeing human keratin fibers, with powerful or chromatic dyeing results that are resistant to washing, perspiration, sebum and light, and that are moreover long-lasting, without impairing said fibers. Furthermore, the colorations obtained using the process give uniform colors from the root to the end of a fiber (little coloration selectivity).

i) Indole or Indoline Compounds

The indole or indoline compound(s) i) as mentioned previously that may be used in the dye composition (A) defined above are preferentially of formula (I) below:

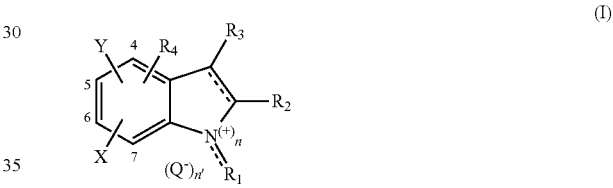

and also the organic or mineral acid or base salts thereof, optical isomers thereof: enantiomers and diastereoisomers, geometrical isomers and tautomers thereof, or an oligomer thereof, and solvates thereof such as hydrates;
in which formula (I):
  $R_1$ represents a hydrogen atom, a radical $(C_1-C_6)$alkyl, $(C_2-C_6)$alkenyl, $(C_1-C_6)$alkylcarbonyl, $(C_2-C_6)$alkenylcarbonyl, $(C_1-C_6)$alkylthiocarbonyl, $(C_2-C_6)$alkenylthiocarbonyl or $R_g$—O—S(O)$_x$—, with $R_g$ representing a hydrogen atom, an alkali metal or alkaline-earth metal, or a $(C_1-C_4)$alkyl and x being 1 or 2, said alkyl or alkenyl groups being optionally substituted, particularly with a heterocyclic group such as heterocycloalkenyl, and said heterocycle being optionally substituted with one or more groups such as carboxyl; preferentially, $R_1$ represents a radical $(C_1-C_4)$alkyl such as methyl or ethyl or the following group:

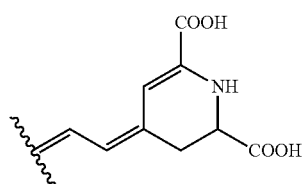 [SMILES: *=C/C=C1\C=C(C(=O)O)NC(C(=O)O)C1]

with n being 1 and ∿∿ representing the point of attachment of the radical to the ammonium N$^+$ of the indolium or of the indolinium (I);

$R_2$ represents a hydrogen atom, a radical $(C_1$-$C_6)$alkyl, or —C(Z)—Z'—$R_a$ such as —C(O)OH or —COO$^-$; with $R_a$ representing a hydrogen atom, an alkali metal or alkaline-earth metal, or a radical $(C_1$-$C_6)$alkyl; Z and Z', which may be identical or different, represent an oxygen or sulfur atom, a group $NR_b$ or $N^+R_bR_c$, $Q'^-$; Z' may also represent a covalent σ bond, with $R_a$, $R_b$ and $R_c$, which may be identical or different, representing a hydrogen atom or a radical $(C_1$-$C_6)$alkyl and $Q'^-$ represents an anionic counterion;

$R_3$ represents:
  i) a hydrogen atom;
  ii) a radical $(C_1$-$C_6)$alkyl optionally substituted especially with a group —$NR_bR_c$, $N^+R_aR_bR_c$, $Q'^-$ or —C(Z)—Z'—$R_a$, with Z, Z', $R_a$, $R_b$, $R_c$ and $Q'^-$ being as defined previously;
  iii) a radical (II)

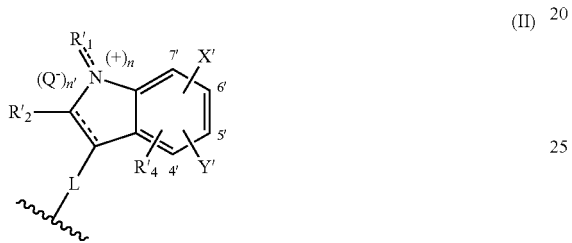

in which radical (II):
  L represents a covalent σ bond, or a divalent group chosen from —Z— and —C(Z)Z'— or a divalent group $(C_1$-$C_6)$alkylene, with Z and Z' as defined previously; particularly, L represents a σ bond,
  $R'_1$, $R'_2$ and $R'_4$ represent the same atoms or radicals as $R_1$, $R_2$ and $R_4$, respectively;
  ⁓ represents the point of attachment of the radical (II) to the rest of the molecule;
preferentially, $R_3$ represents a radical $(C_1$-$C_4)$ alkyl such as methyl or ethyl; an alkylamine radical;
or alternatively $R_1$ and $R_2$ and/or $R_2$ and $R_3$ form, together with the atoms that bear them, a fused, optionally substituted heterocyclic group; or $R_2$ and $R_3$ form, together with the carbon atoms that bear them, a fused, optionally substituted aryl group such as:
  a) benzo optionally substituted especially with groups $(C_1$-$C_4)$alkyl, —OH or —C(Z)Z'$R_a$ such as —C(O)H;
  or b) pyrido optionally substituted with a group $(C_1$-$C_4)$alkyl;

$R_4$ represents:
  i) a hydrogen atom,
  ii) a halogen atom such as chlorine,
  iii) a group —NRR' such as —$NH_2$,
  iv) a group —OH,
  v) a radical $(C_1$-$C_6)$alkyl,
  vi) a radical $(C_1$-$C_6)$alkoxy,
  vii) a radical $(C_1$-$C_6)$alkylthio,
  viii) an aryloxy radical,
  viii) an arylthio radical,
  ix) a radical aryl$(C_1$-$C_6)$alkoxy such as benzoxy,
  x) a radical aryl$(C_1$-$C_6)$alkylthio, and
  xi) a radical $R_aC(Z_a)$—$Z_b$—, with $Z_a$ and $Z_b$ representing an oxygen or sulfur atom or $NR_b$, $R_a$ and $R_b$ being as defined previously;
  xii) a radical (III):

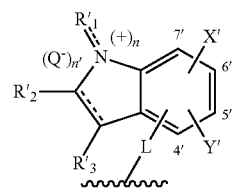

in which radical (III):
  L is as defined previously, particularly L represents a σ bond, more particularly L is in position 4',
  $R'_1$, $R'_2$ and $R'_3$ represent the same atoms or radicals as $R_1$, $R_2$ and $R_3$, respectively;
  ⁓ represents the point of attachment of the radical (III) to the rest of the molecule;
particularly, $R_4$ represents a hydrogen atom;
X and X', which may be identical or different, denote a hydrogen atom or a radical chosen from —NRR' such as —$NH_2$, —$OR_e$, —$SR_e$, $(C_1$-$C_6)$alkyl, and $R_aC(Z_a)$—$Z_b$— as defined previously and $R_e$ representing a hydrogen atom or a group $(C_1$-$C_6)$alkyl, aryl, aryl$(C_1$-$C_6)$alkyl such as benzyl; X and X' preferentially representing a radical —OH or a radical $(C_1$-$C_4)$alkyl such as methyl;
Y and Y', which may be identical or different, denote a group chosen from —$OR'_e$, —$SR'_e$, —NRR' such as —$NH_2$, $R_aC(Z_a)$—$Z_b$— as defined previously, $R_f$—O—S(O)$_x$—$Z_d$— and $R_f$—O—S(O)$_x$—, with $R_f$ representing a hydrogen atom, an alkali metal or alkaline-earth metal, or a $(C_1$-$C_4)$alkyl, $Z_d$ representing an oxygen atom or a group NR with R as defined previously, x as defined previously and $R'_e$ representing the same atoms or radicals as $R_e$; or alternatively the radicals $R_e$ and $R'_e$ of two contiguous groups X and X' and/or contiguous groups Y and Y' form, together with the oxygen or sulfur atom, a heterocyclic group;
the radicals X, Y, X' and Y' being located on any of the carbon atoms 4 to 7 and 4' to 7', respectively; particularly X and Y are in position 5 and 6; X' and Y' are in position 5' and 6' and preferentially X and Y; X' and Y' represent a hydroxyl group or $R_aC(O)$—O— such as acyl-O—;
R and R', which may be identical or different, represent a hydrogen atom or an optionally substituted group $(C_1$-$C_6)$alkyl, such as $(C_1$-$C_4)$alkyl; preferentially, R and R' represent a hydrogen atom;
---- represents a single bond or a double bond;
n is 0 when the bond between $R_1$ and N or $R'_1$ and N is a single bond;
n is 1 when the group $R_1$ or $R'_1$ represents an alkenyl group and when the end connected to the nitrogen atom is a double bond, preferentially, said double bond is conjugated;
$Q^-$ represents an anionic counterion;
n' is 0 or 1;
it being understood that:
  $R_3$ cannot represent the radical (II) when $R_4$ represents a radical (III) and
    when n is 0, then n' is 0, when n is 1, then n' is 1, or n' is 0, in which case a radical —C(Z)Z'—$R_a$ is in the anionic form —C(Z)—Z'$^-$.

According to one particular embodiment of the invention, the compounds of formula (I) are monomers, i.e. $R_3$ represents i) a hydrogen atom; or ii) an optionally substituted radical $(C_1$-$C_6)$alkyl.

According to another preferred embodiment of the invention, the compound(s) of formula (I) are dimers, i.e. $R_3$ represents a radical (II) or $R_4$ represents a radical (III). More particularly, the compound(s) of formula (I) are symmetrical dimers, i.e. they have a C2 axis of symmetry, such as the compound 3,3'-bi-1H-indole-5,5',6,6'-tetrol (40) defined below.

According to one advantageous embodiment of the invention, the compounds of formula (I) are indole compounds with the bond ⸗ between the carbon atoms bearing the radicals $R_2$ and $R_3$ representing a double bond. More particularly, the indole compounds are such that X and/or Y, X' and/or Y' represent a hydroxyl group.

Preferentially, the indole compounds that may be used in the dye composition (A) defined above may correspond to formula (Ia) below:

(Ia)

in which formula (Ia):

$R_1$ and $R_3$, which may be identical or different, represent a hydrogen atom or a $C_1$-$C_4$ alkyl radical;

$R_2$ represents a hydrogen atom or a radical $C_1$-$C_4$ alkyl or —COOH;

X denotes a hydrogen atom, —$NH_2$, —OH, a radical $C_1$-$C_4$ alkyl, a radical $C_1$-$C_4$ alkoxy or a radical —O—C(O)R with R representing H or $C_1$-$C_4$ alkyl such as methyl;

Y denotes —OH, —$NH_2$ or a radical —O—C(O)R, with R as defined previously;

and also the salts of these compounds.

As advantageous indole compounds of formula (I) or (Ia) according to the invention, mention may be made of 5,6-dihydroxyindole, 2-methyl-5,6-dihydroxyindole, 3-methyl-5,6-dihydroxyindole, 4-hydroxyindole, 2,3-dimethyl-5,6-dihydroxyindole, 6-hydroxy-5-methoxyindole, 6-hydroxyindole, 5-hydroxyindole, 7-hydroxyindole, 7-aminoindole, 5-aminoindole, 5,6-dihydroxyindole-2-carboxylic acid, 5-aminoindole, 1-methyl-5,6-dihydroxyindole, 5-acetyloxy-6-hydroxyindole, 6-acetyl-5-hydroxyindole and 5,6-diacetyloxyindole, and the organic or mineral acid or base salts thereof.

According to another variant of the invention, the indole compounds are chosen from the following compounds:

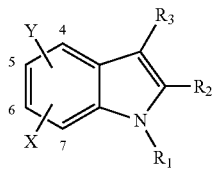

(1)

5,6-dihydroxyindole

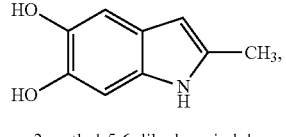

(2)

2-methyl-5,6-dihydroxyindole

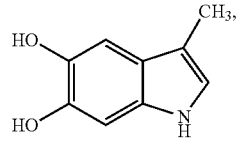

(3)

3-methyl-5,6-dihydroxyindole

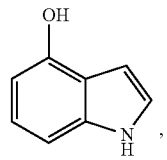

(4)

4-hydroxyindole

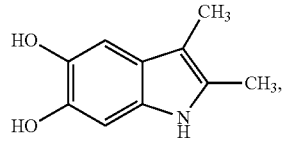

(5)

2,3-dimethyl-5,6-dihydroxyindole

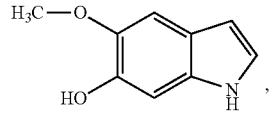

(6)

6-hydroxy-5-methoxyindole

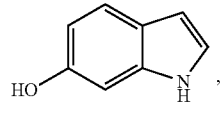

(7)

6-hydroxyindole

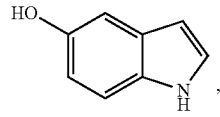

(8)

5-hydroxyindole

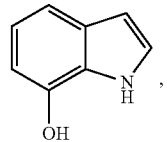

(9)

7-hydroxyindole

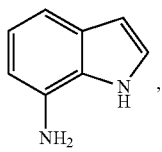

7-aminoindole (10)

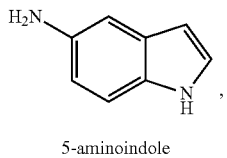

5-aminoindole (11)

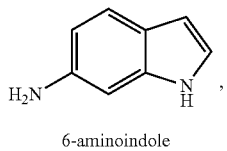

6-aminoindole (12)

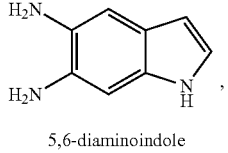

5,6-diaminoindole (13)

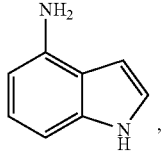

4-aminoindole (14)

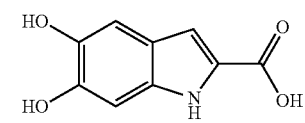

5,6-dihydroxyindole-2-carboxylic acid, or 5,6-dihydroxy-1H-indole-2-carboxylic acid (15)

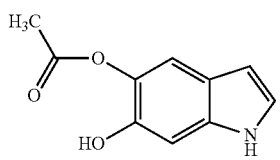

5-acetyloxy-6-hydroxyindole (16)

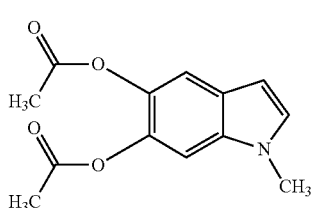

5,6-dimethylcarbonyloxy-1-methyl-1H-indole (17)

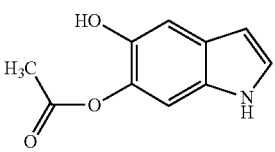

6-acetyloxy-5-hydroxyindole (18)

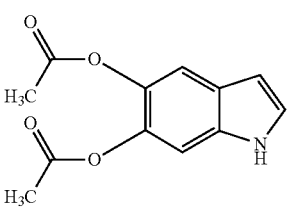

5,6-diacetyloxyindole (19)

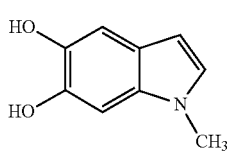

5,6-dihydroxy-1-methyl-1H-indole or 1-methyl-5,6-dihydroxyindole (20)

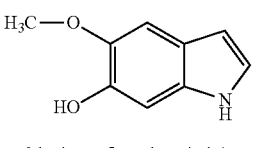

6-hydroxy-5-methoxyindole (21)

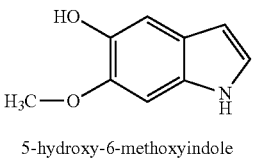

5-hydroxy-6-methoxyindole (22)

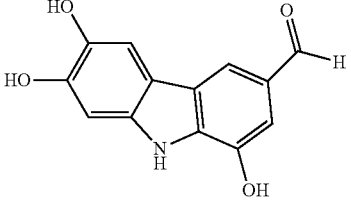

1,6,7-trihydroxy-9H-carbazole-3-carboxaldehyde (23)

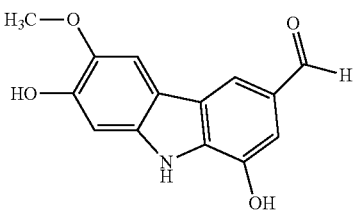

1,7-dihydroxy-6-methoxy-9H-carbazole-3-carboxaldehyde (24)

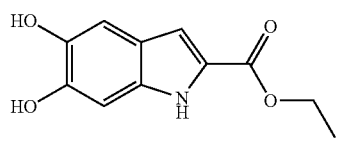
ethyl 5,6-dihydroxy-1H-indole-2-ylcarboxylate
(25)
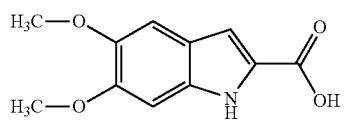
5,6-dimethoxy-1H-indole-2-carboxylic acid
(26)
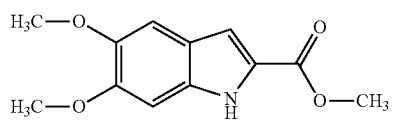
methyl 5,6-dimethoxy-1H-indole-2-ylcarboxylate
(27)
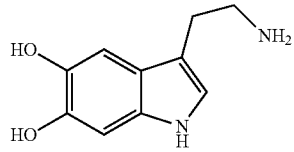
5,6-dihydroxytryptamine
(28)
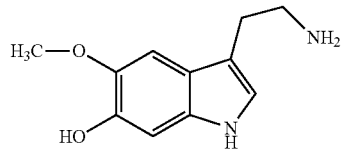
6-hydroxy-5-methoxytryptamine
(29)
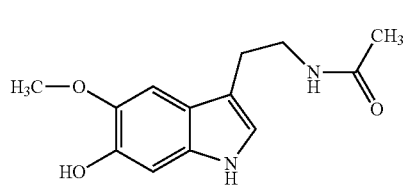
6-hydroxymelatonin
(30)
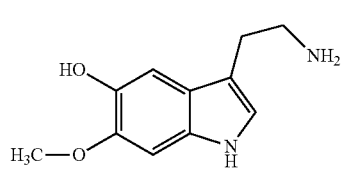
5-hydroxy-6-methoxytryptamine
(31)
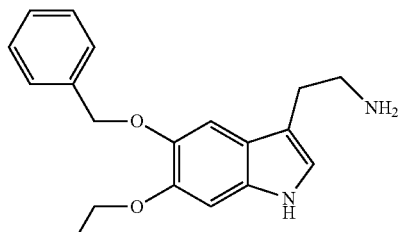
5,6-dibenzoxytryptamine
(32)
Ancorinolate B
(33)
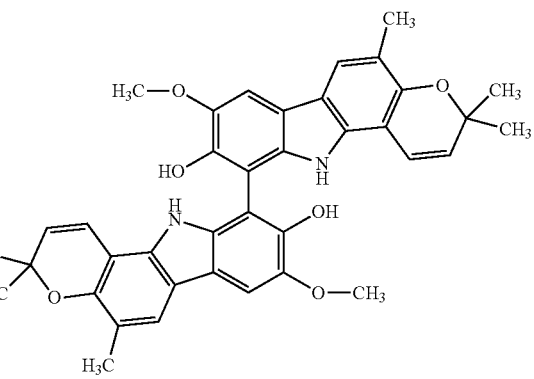
8-8'-bikoenigine
(34)
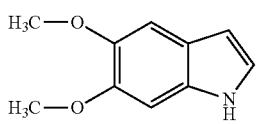
5,6-dimethoxyindole
(35)
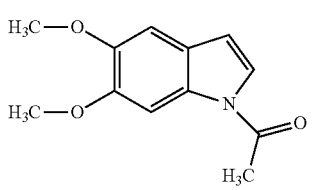
5,6-dimethoxy-1-acetyl-1H-indole
(36)
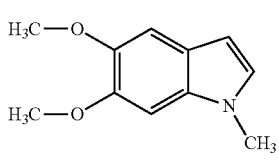
5,6-dimethoxy-1-methyl-1H-indole
(37)

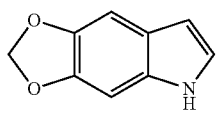

5,6-methylenedioxyindole

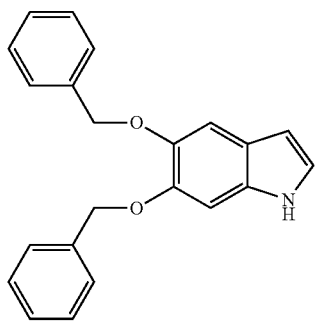

5,6-dibenzoxyindole

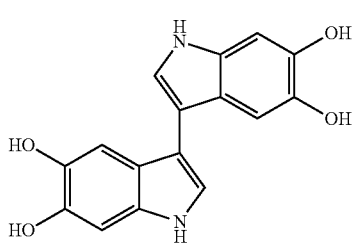

3,3'-bi-1H-indole-5,5',6,6'-tetrol

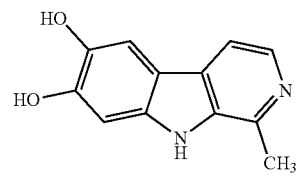

6,7-dihydroxy-1-methyl- -carboline or 1-methyl-9H-pyrido[3,4-b]indole-6,7-diol

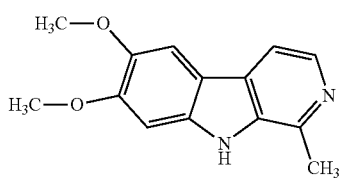

6,7-dimethoxy-1-methyl- -carboline or 1-methyl-9H-pyrido[3,4-b]indole-6,7-dimethoxy

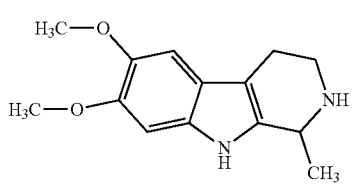

1,2,3,4-tetrahydro-6,7-dimethoxy-1-methyl- -carboline

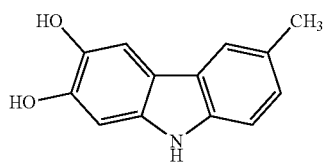

2,3-dihydroxy-6-methyl-9H-carbazole

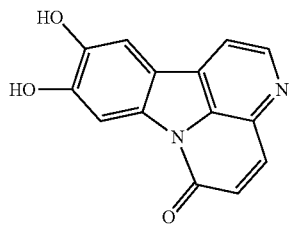

9,10-dihydroxycanthin-6-one

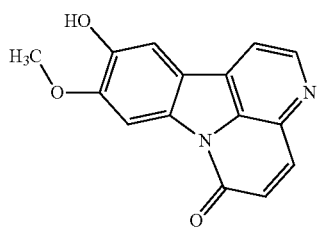

10-hydroxy-9-methoxycanthin-6-one

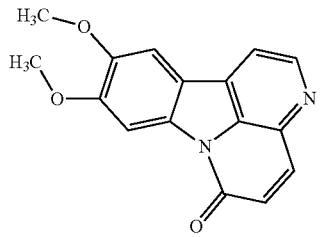

9,10-dimethoxycanthin-6-one

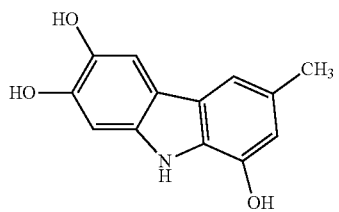

1,6,7-trihydroxy-3-methylcarbazole

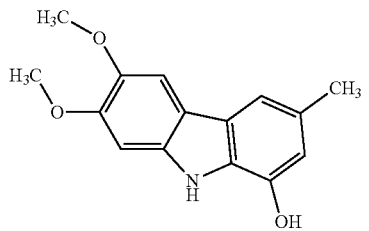

1-hydroxy-6,7-dimethoxy-3-methylcarbazole

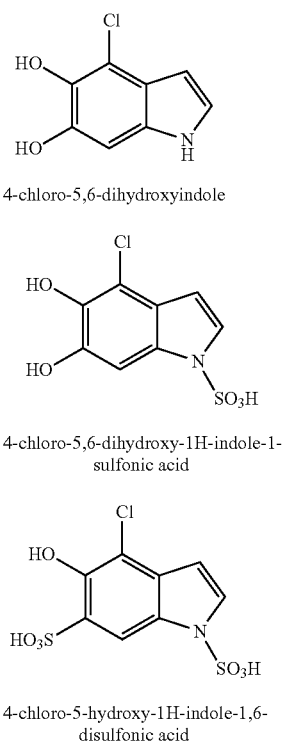

(50) 4-chloro-5,6-dihydroxyindole

(51) 4-chloro-5,6-dihydroxy-1H-indole-1-sulfonic acid

(52) 4-chloro-5-hydroxy-1H-indole-1,6-disulfonic acid and also the organic or mineral acid or base salts thereof.

According to another advantageous embodiment of the invention, the compounds of formula (I) are indole compounds, with the bond ≍ between the carbon atoms bearing the radicals $R_2$ and $R_3$ representing a single bond.

Preferentially, the indole compounds that may be used in the dye composition (A) defined above may correspond to formula (Ib) below:

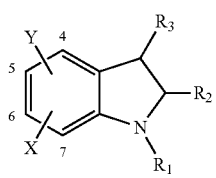

(Ib)

in which formula (Ib) $R_1$, $R_2$, $R_3$, X and Y have the same meanings as those indicated above for the compounds of formula (Ia), and also the enantiomers, diastereoisomers and salts of these compounds.

Among the preferential indoline compounds of formulae (I) and (Ib), mention may be made of 5,6-dihydroxyindoline, N-methyl-5,6-dihydroxyindoline, N-ethyl-5,6-dihydroxyindoline, N-butyl-5,6-dihydroxyindoline, 4-hydroxy-5-methoxyindoline, 6-hydroxy-7-methoxyindoline, 6,7-dihydroxyindoline, 4,5-dihydroxyindoline and 5-methoxy-6-hydroxyindoline, and the organic or mineral acid or base salts thereof.

According to another variant of the invention, the indole compounds are chosen from the compounds of formula (IV), and the decarboxylated form (IV'):

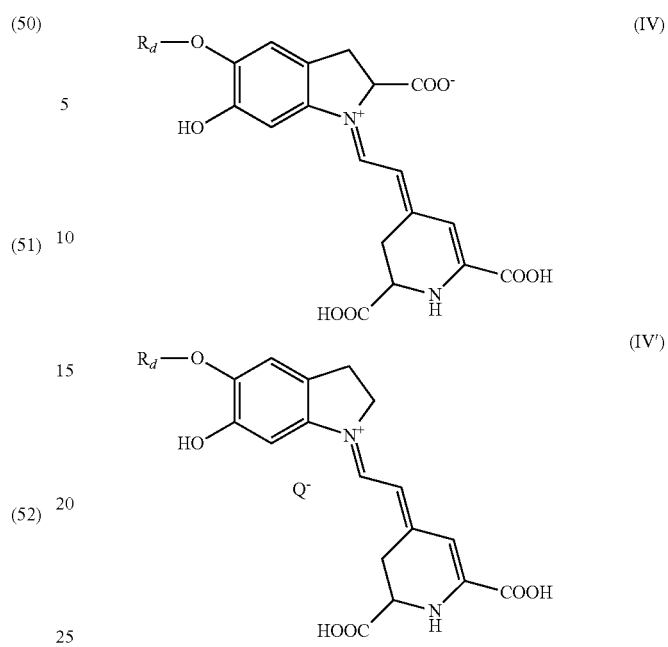

in which formula (IV) $R_d$ represents a hydrogen atom (betanidin or betacyanin), a glucosyl radical (betanin) or a 6'-O-malonylglucosyl radical (phyllocactin), $Q^-$ is an anionic counterion or is absent if one of the carboxyl groups is in anionic form —COO$^-$; and also the enantiomers, diastereoisomers and tautomers thereof, and the organic or mineral acid or base salts thereof.

Preferably, the indole or indoline compounds are chosen from indole compounds, such as those chosen from (1), (2), (3), (5), (7), (8), (16), (18) and (19).

Even more preferentially, the compound of formula (I) is 5,6-dihydroxyindole (1), and also the organic or mineral acid or base salts thereof.

The indole or indoline compounds of the invention may be naturally occurring. The invention may then be performed using one or more natural extracts of animals, bacteria, fungi, algae or plants comprising one or more indole or indoline compounds.

According to the invention, the indole and/or indoline compounds as defined previously are preferably present in a concentration ranging from 0.0005% to 10% by weight relative to the total weight of the dye composition (A). Even more preferentially, this concentration ranges from 0.005% to 5% by weight and better still from 0.01% to 3% by weight, relative to the total weight of the dye composition (A).

For the purposes of the present invention, and unless otherwise indicated:

The saturated or unsaturated, optionally fused rings may also be optionally substituted.

The "alkyl" radicals are linear or branched, saturated hydrocarbon-based radicals, generally of $C_1$-$C_{20}$, particularly of $C_1$-$C_{10}$, preferably $C_1$-$C_6$ alkyl radicals, such as methyl, ethyl, propyl, butyl, pentyl and hexyl.

The "alkenyl" radicals are linear or branched, unsaturated $C_2$-$C_{20}$ hydrocarbon-based radicals; preferably comprising one or more conjugated or unconjugated double bonds, such as ethylene, propylene, butylene, pentylene, 2-methylpropylene, decylene and =CH—CH=.

The "aryl" radicals are fused or nonfused monocyclic or polycyclic carbon-based radicals, preferentially comprising from 6 to 30 carbon atoms, and of which at least one ring is aromatic; the aryl radical is preferentially a phenyl, biphenyl, naphthyl, indenyl, anthracenyl or tetrahydronaphthyl.

The "alkoxy" radicals are alkyl-oxy radicals with alkyl as defined previously, preferably of $C_1$-$C_{10}$ such as methoxy, ethoxy, propoxy and butoxy.

The "alkoxyalkyl" radicals are preferably ($C_1$-$C_{20}$)alkoxy ($C_1$-$C_{20}$)alkyl radicals, such as methoxymethyl, ethoxymethyl, methoxyethyl, ethoxyethyl, etc.

The "cycloalkyl" radicals are generally $C_4$-$C_8$ cycloalkyl radicals, preferably cyclopentyl and cyclohexyl radicals. The cycloalkyl radicals may be substituted cycloalkyl radicals, in particular substituted with alkyl, alkoxy, carboxylic acid, hydroxyl, amine and ketone groups.

The "alkyl" or "alkenyl" radicals, when they are optionally substituted, may be substituted with at least one substituent borne by at least one carbon atom, chosen from:
- a halogen atom;
- a hydroxyl group;
- a $C_1$-$C_2$ alkoxy radical;
- a $C_1$-$C_{10}$ alkoxycarbonyl radical;
- a $C_2$-$C_4$ (poly)hydroxyalkoxy radical;
- an amino radical;
- a quaternary ammonium group —$N^+R'R''R'''$, $M^-$ for which R', R" and R'", which may be identical or different, represent a hydrogen atom or a $C_1$-$C_4$ alkyl group; and $M^-$ represents the counterion of the organic or mineral acid or of the corresponding halide;
- a 5- or 6-membered heterocycloalkyl radical;
- an optionally cationic 5- or 6-membered heteroaryl radical, preferentially imidazolium, optionally substituted with a ($C_1$-$C_4$)alkyl radical, preferentially methyl;
- an amino radical substituted with one or two identical or different $C_1$-$C_6$ alkyl radicals, optionally bearing at least:
  - a hydroxyl group;
  - an amino group optionally substituted with one or two optionally substituted $C_1$-$C_3$ alkyl radicals, said alkyl radicals possibly forming with the nitrogen atom to which they are attached a saturated or unsaturated, optionally substituted 5- to 7-membered heterocycle, optionally comprising at least one other heteroatom identical to or different from nitrogen,
  - a quaternary ammonium group —$N^+R'R''R'''$, $M^-$ as defined previously,
  - or an optionally cationic 5- or 6-membered heteroaryl radical, preferentially imidazolium, optionally substituted with a ($C_1$-$C_4$)alkyl radical, preferentially methyl;
- an acylamino radical (—NR—C(O)R') in which the radical R is a hydrogen atom, a $C_1$-$C_4$ alkyl radical optionally bearing at least one hydroxyl group and the radical R' is a $C_1$-$C_2$ alkyl radical; a carbamoyl radical (($R)_2$N—CO—) in which the radicals R, which may be identical or different, represent a hydrogen atom, a $C_1$-$C_4$ alkyl radical optionally bearing at least one hydroxyl group; an alkylsulfonylamino radical (R'S(O)$_2$—NR—) in which the radical R represents a hydrogen atom, a $C_1$-$C_4$ alkyl radical optionally bearing at least one hydroxyl group and the radical R' represents a $C_1$-$C_4$ alkyl radical or a phenyl radical; an aminosulfonyl radical (($R)_2$N—S(O)$_2$—) in which the radicals R, which may be identical or different, represent a hydrogen atom or a $C_1$-$C_4$ alkyl radical optionally bearing at least one hydroxyl group,
- a carboxylic radical in acid or salified form (preferably with an alkali metal or a substituted or unsubstituted ammonium);
- a cyano group;
- a nitro group;
- a carboxyl or glycosylcarbonyl group;
- a phenylcarbonyloxy group optionally substituted with one or more hydroxyl groups;
- a glycosyloxy group; and
- a phenyl group optionally substituted with one or more hydroxyl groups.

The aryl or heteroaryl or heterocyclic radicals or the aryl or heteroaryl or heterocyclic part of the radicals, when they are optionally substituted, may be substituted with at least one substituent borne by at least one carbon atom, chosen from:
- a $C_1$-$C_{10}$ and preferably $C_1$-$C_8$ alkyl radical optionally substituted with one or more radicals chosen from hydroxyl, $C_1$-$C_2$ alkoxy, $C_2$-$C_4$ (poly)hydroxyalkoxy, acylamino, amino substituted with two $C_1$-$C_4$ alkyl radicals, which may be identical or different, optionally bearing at least one hydroxyl group, or the two radicals possibly forming, with the nitrogen atom to which they are attached, a saturated or unsaturated, optionally substituted 5- to 7-membered and preferably 5- or 6-membered heterocycle optionally comprising another heteroatom identical to or different from nitrogen;
- a halogen atom;
- a hydroxyl group;
- a $C_1$-$C_2$ alkoxy radical;
- a $C_1$-$C_{10}$ alkoxycarbonyl radical;
- a $C_2$-$C_4$ (poly)hydroxyalkoxy radical;
- an amino radical;
- a 5- or 6-membered heterocycloalkyl radical;
- an optionally cationic 5- or 6-membered heteroaryl radical, preferentially imidazolium, optionally substituted with a ($C_1$-$C_4$)alkyl radical, preferentially methyl;
- an amino radical substituted with one or two identical or different $C_1$-$C_6$ alkyl radicals, optionally bearing at least:
  - a hydroxyl group;
  - an amino group optionally substituted with one or two optionally substituted $C_1$-$C_3$ alkyl radicals, said alkyl radicals possibly forming with the nitrogen atom to which they are attached a saturated or unsaturated, optionally substituted 5- to 7-membered heterocycle, optionally comprising at least one other heteroatom identical to or different from nitrogen,
  - a quaternary ammonium group —$N^+R'R''R'''$, $M^-$ for which R', R" and R'", which may be identical or different, represent a hydrogen atom or a $C_1$-$C_4$ alkyl group; and $M^-$ represents the counterion of the organic or mineral acid or of the corresponding halide;
  - or an optionally cationic 5- or 6-membered heteroaryl radical, preferentially imidazolium, optionally substituted with a ($C_1$-$C_4$)alkyl radical, preferentially methyl;
- an acylamino radical (—NR—C(O)R') in which the radical R is a hydrogen atom, a $C_1$-$C_4$ alkyl radical optionally bearing at least one hydroxyl group and the radical R' is a $C_1$-$C_2$ alkyl radical; a carbamoyl radical (($R)_2$N—CO—) in which the radicals R, which may be identical or different, represent a hydrogen atom, a $C_1$-$C_4$ alkyl radical optionally bearing at least one hydroxyl group; an alkylsulfonylamino radical (R'—S(O)$_2$—NR—) in which the radical R represents a hydrogen atom, a $C_1$-$C_4$ alkyl radical optionally bearing at least one hydroxyl group and the radical R' represents a $C_1$-$C_4$ alkyl radical or a phenyl radical; an aminosulfonyl radical (($R)_2$N—S(O)$_2$—) in which the radicals R, which may be identical or different, represent a hydrogen atom or a $C_1$-$C_4$ alkyl radical optionally bearing at least one hydroxyl group, a carboxylic radical in acid or salified form (preferably with an alkali metal or a substituted or unsubstituted ammonium);

a cyano group;

a nitro group;

a polyhaloalkyl group, preferentially trifluoromethyl;

a carboxyl or glycosylcarbonyl group;

a phenylcarbonyloxy group optionally substituted with one or more hydroxyl groups;

a glycosyloxy group; and a phenyl group optionally substituted with one or more hydroxyl groups.

The term "glycosyl radical" means a radical derived from a monosaccharide or polysaccharide.

The radicals containing one or more silicon atoms are preferably polydimethylsiloxane, polydiphenylsiloxane, polydimethylphenylsiloxane or stearoxydimethicone radicals.

The "heterocyclic" radicals are generally cyclic, saturated or unsaturated 3- to 22-membered radicals, comprising in at least one ring one or more heteroatoms chosen from O, N and S, preferably O or N, optionally substituted especially with one or more alkyl, alkoxy, carboxylic acid, hydroxyl, amine or ketone groups. These rings may contain one or more oxo groups on the carbon atoms of the heterocycle of the non-aromatic part. The heterocycles include heteroaryl, heterocycloalkyl or heterocycloalkenyl groups.

The "heterocycloalkyl" radicals represent saturated monocyclic or polycyclic, fused or nonfused, optionally cationic, 3- to 22-membered and preferentially 3- to 7-membered groups, such as morpholinyl, thiomorpholinyl, piperidyl, piperazinyl, pyrrolidinyl, tetrahydrofuryl or azepanyl, preferentially pyrrolidinyl and morpholinyl.

The "heterocycloalkenyl" radicals represent unsaturated monocyclic or polycyclic, fused or nonfused, optionally cationic, 3- to 22-membered and preferentially 5- to 7-membered groups, which comprise from 1 to 3 conjugated or unconjugated double bonds; particularly, the heterocycloalkenyls are piperazenyl such as piperazin-2-en-4-yl, optionally substituted especially with two carboxyl groups in positions 2 and 6 of said heterocycloalkenyl.

The "heteroaryl" radicals represent fused or nonfused, optionally cationic, 5- to 22-membered monocyclic or polycyclic groups, comprising from 1 to 6 heteroatoms chosen from nitrogen, oxygen, sulfur and selenium, and at least one ring of which is aromatic; preferentially, a heteroaryl radical is chosen from acridinyl, benzimidazolyl, benzobistriazolyl, benzopyrazolyl, benzopyridazinyl, benzoquinolyl, benzothiazolyl, benzotriazolyl, benzoxazolyl, pyridyl, tetrazolyl, dihydrothiazolyl, imidazopyridyl, imidazolyl, indolyl, isoquinolyl, naphthoimidazolyl, naphthooxazolyl, naphthopyrazolyl, oxadiazolyl, oxazolyl, oxazolopyridyl, phenazinyl, phenoxazolyl, pyrazinyl, pyrazolyl, pyrilyl, pyrazoyltriazyl, pyridyl, pyridinoimidazolyl, pyrrolyl, quinolyl, tetrazolyl, thiadiazolyl, thiazolyl, thiazolopyridyl, thiazoylimidazolyl, thiopyrylyl, triazolyl, xanthyl and the ammonium salt thereof.

Among the heterocyclic radicals that may be used, mention may be made of furyl, pyranyl, pyrrolyl, imidazolyl, pyrazolyl, pyridyl and thienyl groups.

More preferably, the heterocyclic groups are fused groups such as benzofuryl, chromenyl, xanthenyl, indolyl, isoindolyl, quinolyl, isoquinolyl, chromanyl, isochromanyl, indolidinyl, isoindolinyl, coumarinyl or isocoumarinyl groups, these groups possibly being substituted, in particular with one or more OH groups.

The term "salt of an organic or mineral acid" means a salt derived, for example, from i) hydrochloric acid HCl, ii) hydrobromic acid HBr, iii) sulfuric acid $H_2SO_4$, iv) alkylsulfonic acids: Alk-S(O)$_2$OH such as methanesulfonic acid and ethanesulfonic acid; v) arylsulfonic acids: Ar—S(O)$_2$OH such as benzenesulfonic acid and toluenesulfonic acid; vi) citric acid; vii) succinic acid; viii) tartaric acid; ix) lactic acid; x) alkoxysulfinic acids: Alk-O—S(O)OH such as methoxysulfinic acid and ethoxysulfinic acid; xi) aryloxysulfinic acids such as tolueneoxysulfinic acid and phenoxysulfinic acid; xii) phosphoric acid P(O)(OH)$_3$; xiii) acetic acid $CH_3$C(O)OH; xiv) triflic acid $CF_3$S(O)$_2$OH; and xv) tetrafluoroboric acid $HBF_4$.

The term "salt of an organic or mineral base" means a salt derived, for example, from mineral bases such as i) sodium hydroxide NaOH, ii) potassium hydroxide KOH, or from organic bases such as iii) aqueous ammonia; iv) amines and hydroxyamines such as (tri)($C_1$-$C_6$)alkylamine, (tri)hydroxy($C_1$-$C_6$)alkylamine, or v) salts derived from alkali metals and alkaline-earth metals.

The "anionic counterions" are anions or anionic groups associated with the cationic charge of the dye; more particularly, the anionic counterion is chosen from: i) halides such as chloride or bromide; ii) nitrates; iii) sulfonates, including $C_1$-$C_6$ alkylsulfonates: Alk-S(O)$_2$O$^-$ such as methanesulfonate or mesylate, and ethanesulfonate; iv) arylsulfonates: Ar—S(O)$_2$O$^-$ such as benzenesulfonate and toluenesulfonate or tosylate; v) citrate; vi) succinate; vii) tartrate; viii) lactate; ix) alkyl sulfates: Alk-O—S(O)O$^-$ such as methyl sulfate and ethyl sulfate; x) aryl sulfates: Ar—O—S(O)O$^-$ such as benzene sulfate and toluene sulfate; xi) alkoxy sulfates: Alk-O—S(O)$_2$O$^-$ such as methoxy sulfate and ethoxy sulfate; xii) aryloxy sulfates: Ar—O—S(O)$_2$O$^-$; xiii) phosphate; xiv) acetate; xv) triflate; and xvi) borates such as a tetrafluoroborate.

Additional Ortho-Diphenols

In the process of the invention, the indole and/or indoline compounds as defined previously may be used in combination with ortho-diphenols, other than the indole and indoline compounds, comprising at least one aromatic ring, preferably a benzene ring, comprising at least two hydroxyl groups (OH) borne by two adjacent carbon atoms of the aromatic ring.

The aromatic ring may more particularly be a fused aryl or fused heteroaryl ring, i.e. optionally containing one or more heteroatoms, such as benzene, naphthalene, tetrahydronaphthalene, indane, indene, anthracene, phenanthrene, isoindole, indoline, isoindoline, benzofuran, dihydrobenzofuran, chroman, isochroman, chromene, isochromene, quinoline, tetrahydroquinoline and isoquinoline, said aromatic ring comprising at least two hydroxyl groups borne by two adjacent carbon atoms of the aromatic ring. Preferentially, the aromatic ring of the ortho-diphenol derivatives according to the invention is a benzene ring.

The term "fused ring" means that at least two saturated or unsaturated, heterocyclic or non-heterocyclic rings have a common bond, i.e. at least one ring is fused to another ring.

The additional ortho-diphenols according to the invention may or may not be salified. They may also be in aglycone form (without attached sugar) or in the form of glycosylated compounds.

More particularly, the ortho-diphenol derivatives represent compounds of formula (II), other than the indole and indoline compounds as defined previously, or an oligomer thereof, in salified or non-salified form:

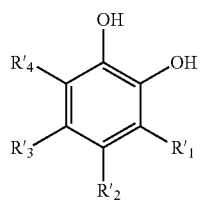

in which formula (II) the substituents:
$R'_1$ to $R'_4$, which may be identical or different, represent:
a hydrogen atom,
a halogen atom,
a hydroxyl radical,
a carboxyl radical,
an alkyl carboxylate or alkoxycarbonyl radical,
an optionally substituted amino radical,
an optionally substituted linear or branched alkyl radical,
an optionally substituted linear or branched alkenyl radical,
an optionally substituted cycloalkyl radical,
an alkoxy radical,
an alkoxyalkyl radical,
an alkoxyaryl radical, the aryl group possibly being optionally substituted,
an aryl radical,
a substituted aryl radical,
a saturated or unsaturated heterocyclic radical, optionally bearing a cationic or anionic charge, optionally substituted and/or optionally fused with an aromatic ring, preferably a benzene ring, said aromatic ring being optionally substituted particularly with one or more hydroxyl or glycosyloxy groups,
a radical containing one or more silicon atoms,
in which two of the substituents borne by two adjacent carbon atoms $R'_1$-$R'_2$, $R'_2$-$R'_3$ or $R'_3$-$R'_4$ form, together with the carbon atoms that bear them, a saturated or unsaturated, aromatic or non-aromatic ring, optionally containing one or more heteroatoms and optionally fused with one or more saturated or unsaturated rings optionally containing one or more heteroatoms. Particularly, $R'_1$ to $R'_4$ together form from one to four rings.

One particular embodiment of the invention concerns ortho-diphenol derivatives of formula (II) in which two adjacent substituents $R'_1$-$R'_2$, $R'_2$-$R'_3$ or $R'_3$-$R'_4$ cannot form, with the carbon atoms that bear them, a pyrrolyl or pyrrolidinyl radical. More particularly, $R'_2$ and $R'_3$ cannot form a pyrrolyl or pyrrolidinyl radical fused to the benzene ring bearing the two hydroxyl groups.

The additional ortho-diphenols that are useful in the process of the invention may be natural or synthetic. Among the additional natural ortho-diphenols are compounds that may be present in nature and that are reproduced by chemical (semi)synthesis.

The ortho-diphenol salts of the invention may be salts of acids or bases. The acids may be mineral or organic. Preferably, the acid is hydrochloric acid, which leads to chlorides.

The bases may be mineral or organic. In particular, the bases are alkali metal hydroxides such as sodium hydroxide, which leads to sodium salts.

According to one particular embodiment of the invention, the composition comprises as ingredient i) one or more synthetic ortho-diphenol derivatives that do not exist in nature.

According to another embodiment of the invention, the process for dyeing keratin fibers uses one or more additional natural ortho-diphenol derivatives other than the indole and indoline compounds as defined previously.

More particularly, the additional ortho-diphenols that may be used in the process of the invention are in particular:
flavanols, for instance catechin and epicatechin gallate,
flavonols, such as quercetin,
anthocyanidins, for instance cyanidin, delphinidin and petunidin,
anthocyanins or anthocyans, for instance myrtillin,
ortho-hydroxybenzoates, for example gallic acid salts,
flavones, such as luteolin,
hydroxystilbenes, for example tetrahydroxy-3,3',4,5'-stilbene, optionally oxylated (for example glucosylated),
3,4-dihydroxyphenylalanine and derivatives thereof,
2,3-dihydroxyphenylalanine and derivatives thereof,
4,5-dihydroxyphenylalanine and derivatives thereof,
dihydroxycinnamates such as caffeic acid and chlorogenic acid,
ortho-polyhydroxycoumarins,
ortho-polyhydroxyisocoumarins,
ortho-polyhydroxycoumarones,
ortho-polyhydroxyisocoumarones,
ortho-polyhydroxychalcones,
ortho-polyhydroxychromones,
ortho-polyhydroxyquinones,
ortho-polyhydroxyxanthones,
1,2-dihydroxybenzene and derivatives thereof,
1,2,4-trihydroxybenzene and derivatives thereof,
1,2,3-trihydroxybenzene and derivatives thereof,
2,4,5-trihydroxytoluene and derivatives thereof,
proanthocyanidins and especially the proanthocyanidins A1, A2, B1, B2, B3 and C1,
proanthocyanins,
tannic acid,
ellagic acid,
ortho-hydroxycoumestanes,
ortho-hydroxypterocarpanes,
ortho-hydroxyneoflavans
and mixtures of the preceding compounds.

When the dye precursors have D and L forms, the two forms may be used in the compositions according to the invention, as may the racemic mixtures.

According to one embodiment, the additional natural ortho-diphenols are derived from extracts of animals, bacteria, fungi, algae or plants, used in their entirety or partially. In particular as regards plants, the extracts are derived from plant or plant parts such as fruit, including citrus fruit, legumes, trees and shrubs. Mixtures of these extracts that are rich in ortho-diphenols as defined previously may also be used.

Preferably, the additional natural ortho-diphenol(s) of the invention are derived from extracts of plants or plant parts.

For the purposes of the invention, said extracts will be assimilated in their entirety as compound i).

The extracts are obtained by extraction of various plant parts, for instance the root, the wood, the bark, the leaf, the flower, the fruit, the seed, the clove or the peel.

Among the plant extracts, mention may be made of extracts of tea leaves and of rose.

Among the fruit extracts, mention may be made of extracts of apple, of grape (in particular of grape seed) or extracts of cocoa beans and/or pods.

Among the legume extracts, mention may be made of extracts of potato or of onion peel.

Among the extracts of tree wood, mention may be made of extracts of pine bark, extracts of campeachy wood, extracts of quebracho wood, extracts of braziletto wood and extracts of gall nuts.

Mixtures of plant extracts may also be used.

According to one particular embodiment of the invention, the additional ortho-diphenol derivative(s) are natural extracts, rich in ortho-diphenols. According to one preferred mode, the additional ortho-diphenol derivative(s) are solely natural extracts.

The natural extracts according to the invention may be in the form of powders or liquids. Preferably, the extracts of the invention are in the form of powders.

According to the invention, the synthetic, natural ortho-diphenol derivative(s), and/or the natural extract(s) used containing them preferably represent from 0.001% to 20% by weight relative to the total weight of composition (A).

As regards the pure additional ortho-diphenols, the content in composition (A) containing them is preferably between 0.001% and 5% by weight of each of this composition.

As regards the extracts, the content in composition (A) containing the extracts per se is preferably between 0.5% and 20% by weight of this composition.

ii) Metal Salt

The process of the invention uses one or more ingredients that are metal salts.

Particularly, the metal salts are chosen from manganese (Mn) and zinc (Zn) salts.

For the purposes of the present invention, the term "salts" means the oxides of these metals and salts per se derived especially from the action of an acid on a metal. Preferably, the salts are not oxides. Among the salts, mention may be made of halides such as chlorides, fluorides and iodides; sulfates, phosphates; nitrates; perchlorates and carboxylic acid salts and polymer complexes that can support said salts, and also mixtures thereof.

More particularly, manganese salt is other than or manganese carbonate, manganese hydrogen carbonate or manganese dihydrogen carbonate.

As examples of polymer complexes that can support said salts, mention may be made of manganese pyrrolidone carboxylate.

The carboxylic acid salts that may be used in the invention also include salts of hydroxylated carboxylic acids such as gluconate.

By way of example, mention may be made of manganese chloride, manganese fluoride, manganese acetate tetrahydrate, manganese lactate trihydrate, manganese phosphate, manganese iodide, manganese nitrate trihydrate, manganese bromide, manganese perchlorate tetrahydrate, manganese sulfate monohydrate and manganese gluconate. The salts advantageously used are manganese gluconate and manganese chloride.

Among the zinc salts, mention may be made of zinc sulfate, zinc gluconate, zinc chloride, zinc lactate, zinc acetate, zinc glycinate and zinc aspartate.

The manganese and zinc salts may be introduced in solid form into the compositions or may be derived from a natural, mineral or spring water that is rich in these ions or alternatively from seawater (especially the Dead Sea). They may also originate from mineral compounds, for instance earths, ochres such as clays (for example green clay) or even from a plant extract containing them (cf. for example patent FR 2 814 943).

Particularly, the metal salts of the invention are in oxidation state II, such as Mn (II) and Zn (II).

Even more preferentially, the metal salt of the invention is a manganese salt and more particularly Mn(II).

According to one preferred embodiment of the invention, the metal salts used represent from 0.001% to 10% by weight approximately relative to the total weight of the composition(s) containing this or these metal salts, and even more preferentially from 0.05% to 0.1% by weight approximately.

iii) Hydrogen Peroxide or Systems that Generate Hydrogen Peroxide

In the context of the present invention, the third constituent of composition (A) or of the process is iii) hydrogen peroxide or one or more systems that generate hydrogen peroxide, such as:

a) urea peroxide;
b) polymeric complexes that can release hydrogen peroxide, such as polyvinyl pyrrolidone/$H_2O_2$ in particular in the form of powders, and the other polymeric complexes described in U.S. Pat. No. 5,008,093; U.S. Pat. No. 3,376,110; U.S. Pat. No. 5,183,901;
c) oxidases that produce hydrogen peroxide in the presence of a suitable substrate (for example glucose in the case of glucose oxidase or uric acid with uricase);
d) metal peroxides that generate hydrogen peroxide in water, for instance calcium peroxide or magnesium peroxide;
e) perborates; or
f) percarbonates.

According to one preferred embodiment of the invention, the composition contains one or more systems that generate hydrogen peroxide, chosen from a) urea peroxide, b) polymeric complexes that can release hydrogen peroxide, chosen from polyvinylpyrrolidone/$H_2O_2$; c) oxidases; e) perborates and f) percarbonates.

Particularly, the third constituent of composition (A) is hydrogen peroxide.

According to one particular mode of the invention, the hydrogen peroxide used or the system(s) used that generate hydrogen peroxide preferably represent from 0.001% to 12% by weight expressed as hydrogen peroxide relative to the total weight of the composition(s) containing them, and even more preferentially from 0.2% to 2.7% by weight.

iv) Basifying Agents

Composition (B) of the process of the invention comprises one or more basifying agents.

The basifying agent(s) may be mineral or organic.

Among the organic basifying agents, mention may be made of organic amines and in particular alkanolamines such as monoethanolamine, diethanolamine, triethanolamine, 2-amino-2-methyl-1-propanol, amino acids, in particular basic amino acids such as lysine and arginine, and optionally substituted alkylenediamines of formula (V) below:

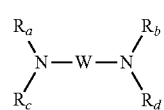

(V)

in which W is a propylene residue optionally substituted with a hydroxyl group or a $C_1$-$C_4$ alkyl radical; $R_a$, $R_b$, $R_c$ and $R_d$, which may be identical or different, represent a hydrogen atom or a $C_1$-$C_4$ alkyl or $C_1$-$C_4$ hydroxyalkyl radical; for instance diamines such as diaminopropane.

Preferably, the organic basifying agent(s) are chosen from basic amino acids. More preferentially, the organic basifying agent is arginine.

Among the mineral basifying agents, mention may be made of aqueous ammonia, alkali metal or alkaline-earth metal hydroxides, phosphates, monohydrogen phosphates and (bi)carbonates.

In the context of the present invention, the preferred basifying agent is chosen from (bi)carbonates.

The term "(bi)carbonates" means:

a) carbonates of alkali metals ($Met_2^+$, $CO_3^{2-}$), of alkaline-earth metals ($Met'^{2+}$, $CO_3^{2-}$) of ammonium (($R''_4N^+)_2$, $CO_3^{2-}$) or of phosphonium (($R''_4P^+)_2$, $CO_3^{2-}$, with Met' representing an alkaline-earth metal and Met representing an alkali metal, and R", which may be identical or different, represent a hydrogen atom, an optionally substituted group ($C_1$-$C_6$)alkyl such as hydroxyethyl), and b) bicarbonates, also known as hydrogen carbonates, of the following formulae:

$R'^+$, $HCO_3^-$, with R' representing a hydrogen atom, an alkali metal, an ammonium group $R''_4N^+$— or a phosphonium group $R''_4P^+$— in which R", which may be identical or different, represent a hydrogen atom, an optionally substituted group ($C_1$-$C_6$)alkyl such as hydroxyethyl and, when R' represents a hydrogen atom, the hydrogen carbonate is then known as a dihydrogen carbonate ($CO_2$, $H_2O$); and $Met'^{2+}$ $(HCO_3^-)_2$, with Met' representing an alkaline-earth metal.

More particularly, the alkaline agent is chosen from alkali metal or alkaline-earth metal (bi)carbonates; preferentially alkali metal (bi)carbonates.

Mention may be made of Na, K, Mg and Ca carbonates or hydrogen carbonates and mixtures thereof, and in particular sodium hydrogen carbonate. These hydrogen carbonates may originate from a natural water, for example source water of the Vichy basin, La Roche Posay water, or Badoit water (cf. for example patent FR 2 814 943). Particularly, mention may be made of sodium carbonate [497-19-8]=$Na_2CO_3$, sodium hydrogen carbonate or sodium bicarbonate [144-55-8]=$NaHCO_3$, and sodium dihydrogen carbonate=Na $(HCO_3)_2$.

In one particular variant of the invention, composition (B) comprises one or more mineral basifying agents and one or more organic basifying agents.

More preferentially, composition (B) comprises one or more (bi)carbonates and one or more basic amino acids such as arginine.

According to the invention, the basifying agent(s) used preferably represent from 0.001% to 10% by weight relative to the total weight of composition (B), and even more preferentially from 0.005% to 5% by weight.

vi) Cosmetic Compositions

The cosmetic compositions according to the invention are cosmetically acceptable, i.e. they comprise a dye support that generally contains water or a mixture of water and of one or more organic solvents or a mixture of organic solvents.

The term "organic solvent" means an organic substance that is capable of dissolving or dispersing in another substance without chemically modifying it.

Organic Solvents:

Examples of organic solvents that may be mentioned include $C_1$-$C_4$ lower alcohols, such as ethanol and isopropanol; polyols and polyol ethers such as 2-butoxyethanol, propylene glycol, propylene glycol monomethyl ether, diethylene glycol monoethyl ether and monomethyl ether, hexylene glycol, and also aromatic alcohols, for instance benzyl alcohol or phenoxyethanol.

The organic solvents are present in proportions preferably of between 1% and 40% by weight approximately and even more preferentially between 5% and 30% by weight approximately relative to the total weight of the dye composition.

Adjuvants:

The composition(s) of the dyeing process in accordance with the invention may also contain various adjuvants conventionally used in hair dye compositions, such as anionic, cationic, nonionic, amphoteric or zwitterionic surfactants or mixtures thereof, anionic, cationic, nonionic, amphoteric or zwitterionic polymers or mixtures thereof, mineral or organic thickeners, and in particular anionic, cationic, nonionic and amphoteric polymeric associative thickeners, antioxidants, penetrants, sequestrants, fragrances, buffers, dispersants, conditioning agents, for instance volatile or non-volatile, modified or unmodified silicones, film-forming agents, ceramides, preserving agents and opacifiers.

Said adjuvants are preferably chosen from surfactants such as anionic or nonionic surfactants or mixtures thereof and mineral or organic thickeners.

The above adjuvants are generally present in an amount for each of them of between 0.01% and 40% by weight relative to the weight of the composition, and preferably between 0.1% and 20% by weight relative to the weight of the composition.

Needless to say, a person skilled in the art will take care to select this or these additional compound(s) such that the advantageous properties intrinsically associated with the composition(s) that is (are) useful in the reshaping process in accordance with the invention are not, or are not substantially, adversely affected by the envisioned addition(s).

Additional Dyes:

The process using compositions (A) and (B) and ingredients i) to iv) as defined previously may also use or comprise one or more additional direct dyes. These direct dyes are chosen, for example, from those conventionally used in direct dyeing, and among which mention may be made of any commonly used aromatic and/or non-aromatic dye such as neutral, acidic or cationic nitrobenzene direct dyes, neutral, acidic or cationic azo direct dyes, natural direct dyes other than ortho-diphenols, neutral, acidic or cationic quinone and in particular anthraquinone direct dyes, azine, triarylmethane, indoamine, methine, styryl, porphyrin, metalloporphyrin, phthalocyanine, cyanine and methine direct dyes, and fluorescent dyes. All these additional dyes are other than the ortho-diphenol derivatives according to the invention.

Among the natural direct dyes, mention may be made of lawsone, juglone, indigo, isatin, curcumin, spinulosin, apigenidin and orceins. Extracts or decoctions containing these natural dyes, and in particular henna-based poultices or extracts, may also be used.

The additional direct dye(s) used in the composition(s) preferably represent from 0.001% to 10% by weight approximately relative to the total weight of the composition(s) containing them, and even more preferentially from 0.05% to 5% by weight approximately.

The compositions of the process using ingredients i) to iv) as defined previously may also use or comprise one or more oxidation bases and/or one or more couplers conventionally used for the dyeing of keratin fibers.

Among the oxidation bases, mention may be made of para-phenylenediamines, bis(phenyl)alkylenediamines, para-aminophenols, bis-para-aminophenols, ortho-aminophenols and heterocyclic bases, and the addition salts thereof.

Among these couplers, mention may be made especially of meta-phenylenediamines, meta-aminophenols, meta-diphenols, naphthalene-based couplers and heterocyclic couplers, and the addition salts thereof.

The oxidation base(s) present in the composition(s) are each generally present in an amount of between 0.001% and 10% by weight relative to the total weight of the corresponding compositions.

The cosmetic composition(s) of the invention may be in various galenical forms, such as a powder, a lotion, a mousse, a cream or a gel, or in any other form that is suitable for dyeing keratin fibers. They may also be conditioned in a pump-dispenser bottle without a propellant or under pressure in an aerosol can in the presence of a propellant and form a mousse.

pH of the Composition(s)

According to one particular mode of the invention, the pH of the composition(s) containing the basifying agent(s) is greater than 7 and preferably between 8 and 12. It is particularly between 8 and 10.

The pH of the composition containing hydrogen peroxide or a system that generates hydrogen peroxide, i.e. composition (A), is preferably less than 7, more particularly between 1 and 5.

The pH of these compositions may be adjusted to the desired value by means of acidifying or basifying agents usually used in the dyeing of keratin fibers, or alternatively using standard buffer systems.

Among the acidifying agents for the compositions used in the invention, examples that may be mentioned include mineral or organic acids, for instance hydrochloric acid, orthophosphoric acid or sulfuric acid, carboxylic acids, for instance acetic acid, tartaric acid, citric acid and lactic acid, and sulfonic acids.

vii) Dyeing Process

The dyeing process of the invention is a process in which keratin fibers, more particularly human keratin fibers such as the hair, are treated:
with a composition (A) comprising
i) one or more indole or indoline compounds,
ii) one or more metal salts,
iii) hydrogen peroxide or one or more systems that generate hydrogen peroxide; and then
with a composition (B) comprising iv) one or more basifying agents.

The leave-on time after application of compositions (A) and (B) is set at between 3 and 120 minutes, preferentially between 10 and 60 minutes and more preferentially between 15 and 45 minutes.

The keratin fibers may or may not be moistened beforehand.

According to one particular dyeing process of the invention, said process may be followed by post-treatment steps such as shampooing using a standard shampoo, rinsing, for example with water, and/or drying the keratin fibers by heat treatment as defined below.

Preferentially, said process does not involve intermediate rinsing between the applications of compositions (A) and (B).

Preferably, between the application of composition (A) and the application of composition (B) of the dyeing process of the invention, the fibers are:
a) either wiped mechanically as described below,
b) or dried by heat with a heat treatment as described below,
c) or not rinsed, i.e. steps 1 and 2 are performed successively.

According to a particularly preferred process of the invention, just before the step that uses ingredient iv), the fibers are
a) mechanically wiped.

More preferentially, between the first and second step, the fibers are wiped, preferentially using a towel or absorbent paper, or are dried by heat with a heat treatment at a temperature particularly between 60 and 220° C. and preferably between 120 and 200° C.

Irrespective of the application method, the application temperature is generally between room temperature (15 to 25° C.) and 80° C. and more particularly between 15 and 45° C. Thus, after application of the composition according to the invention, the head of hair may advantageously be subjected to a heat treatment by heating to a temperature of between 30 and 60° C. In practice, this operation may be performed using a styling hood, a hairdryer, an infrared ray dispenser or other standard heating appliances.

It is possible to use, both as heating means and as hair straightening means, a heating iron at a temperature of between 60 and 220° C. and preferably between 120 and 200° C.

One particular mode of the invention concerns a dyeing process that is performed at room temperature (25° C.).

In all the particular modes and variants of the processes described previously, the mentioned compositions (A) and (B) are ready-to-use compositions that may result from the extemporaneous mixing of two or more compositions and especially of compositions present in dyeing kits. This is especially true for composition (A), which may be derived from the mixing of a composition (A1) comprising iii) hydrogen peroxide or one or more systems that generate hydrogen peroxide and a composition (A2) comprising i) one or more indole or indoline compounds as defined previously, and ii) one or more metal salts.

viii) Step(s) of Mechanical Wiping and/or Drying

According to one particular mode of the invention, the process for dyeing keratin fibers comprises at least one intermediate step of mechanical wiping of the fibers and/or of drying and/or non-rinsing. The steps of intermediate mechanical wiping and drying are also known as "controlled non-rinsing" to distinguish from "standard abundant rinsing with water" and "non-rinsing".

The term "mechanical wiping of the fibers" means rubbing an absorbent article on the fibers and physical removal, by means of the absorbent article, of the excess ingredient(s) that have not penetrated the fibers. The absorbent article may be a piece of fabric such as a towel, particularly a terry towel, a cloth or absorbent paper such as household roll towel.

According to one particularly advantageous process of the invention, the mechanical wiping is performed without total drying of the fiber, leaving the fiber moist.

The term "drying" means the action of evaporating the organic solvents and/or water that are in one or more compositions used in the process of the invention, comprising or not comprising one or more ingredients i) to iv) as defined previously. The drying may be performed with a source of heat (convection, conduction or radiation) by sending, for example, a stream of hot gas such as air necessary to evaporate the solvent(s). Sources of heat that may be mentioned include a hairdryer, a hairstyling hood, a hair-straightening iron, an infrared ray dispenser or other standard heating appliances.

ix) Dyeing Device or "Kit"

Another subject of the invention is a multi-compartment dyeing device or "kit". Advantageously, this kit comprises from 2 to 5 compartments containing from 2 to 5 compositions in which are distributed i) one or more indole or indoline compounds as defined previously, ii) one or more metal salts, iii) hydrogen peroxide or one or more systems that generate hydrogen peroxide, and iv) one or more (bi)carbonates.

According to a first variant, the kit comprises four compartments, the first compartment comprising a cosmetic composition containing i) one or more indole or indoline compounds as defined previously, the second compartment comprising a composition containing ii) one or more metal salts, the third compartment comprising a composition containing iii) hydrogen peroxide or one or more systems that generate hydrogen peroxide, and the fourth compartment containing a composition containing iv) one or more basifying agents.

Another preferred embodiment concerns a device comprising three compartments:
(a) a first compartment contains a composition containing:
  i) one or more indole or indoline compounds as defined previously; and
(b) a second compartment contains a composition containing:
  ii) one or more metal salts,
  iii) hydrogen peroxide or one or more systems that generate hydrogen peroxide;
(c) a third compartment contains iv) one or more basifying agents.

In this other embodiment, at least one of the three compositions is preferably aqueous and the indole or indoline compounds as defined previously may be in powder form.

It is also possible to have a kit containing three compartments, the first a) containing a composition comprising i) one or more indole or indoline compounds as defined previously and ii) one or more metal salts, the second b) containing a composition comprising iii) hydrogen peroxide or a system that generates hydrogen peroxide, and the third c) containing a composition comprising iv) one or more basifying agents. In this other kit, at least one of the compositions is preferably aqueous. This composition preferably contains hydrogen peroxide.

According to one particular mode of the invention, the kit comprises two compartments: a first compartment comprising a composition containing i) one or more indole or indoline compounds as defined previously, ii) one or more metal salts, iii) hydrogen peroxide or one or more systems that generate hydrogen peroxide, and the second compartment containing iv) one or more basifying agents.

Among the two-compartment kits, it is also possible to have kits that contain, in a first compartment, a composition comprising compounds i), ii) and iv) as defined previously and, in a second compartment, a composition comprising compound iii) as defined previously.

In these two variants of two-compartment kits, the first composition contained in the first compartment comprising either i), ii) and iii) or i), ii) and iv) is in powder form and, preferably, the second composition is aqueous.

According to one variant, the device according to the invention also comprises an additional composition (c) comprising one or more treating agents.

The compositions of the device according to the invention are conditioned in separate compartments, optionally accompanied by suitable application means, which may be identical or different, such as fine brushes, coarse brushes or sponges.

The device mentioned above may also be equipped with a means for dispensing the desired mixture on the hair, such as the devices described in patent FR 2 586 913.

EXAMPLES OF DYEING

Compositions A and B were prepared as follows:

| Composition A | A1 Comparative | A2 Invention |
|---|---|---|
| 5,6-Dihydroxyindole, | 0.25 g | 0.25 g |
| Hexylene glycol | 5 g | 5 g |
| ($C_8$-$C_{10}$)Alkyl polyglucoside (60% AM) | 10.33 g | 10.33 g |
| Manganese gluconate (i.e. 0.006 weight % equivalent metal $Mn^{2+}$) | 0.05 g | 0.05 g |
| Hydrogen peroxide | — | 1.2 g |
| Demineralized water | qs 100 g | qs 100 g |

| Composition B | B1 | B2 |
|---|---|---|
| Sodium bicarbonate | 5 g | 5 g |
| Hydrogen peroxide | 1.2 g | — |
| Demineralized water | qs 100 g | qs 100 g |

For Tests 1 and 2:

Composition A is applied to locks of permanent-waved dry hair containing 90% white hairs, with a bath ratio of 5 g of formula per 1 g of hair. The composition is then left to stand on the locks for 30 minutes at room temperature.

After this, the hair impregnated with the first composition is wiped using an absorbent paper towel to remove the excess formula.

Composition B is then applied to the hair with a bath ratio of 4 g per 1 g of lock; the leave-on time is 2 minutes at room temperature. After a few minutes, a very intense coloration appears.

Colorimetric Results:

The coloration of the hair is evaluated visually and read on a Minolta spectrocolorimeter (CM3600d, illuminant D65, angle 10°, SCI values) for the L*, a*, b* colorimetric measurements.

In this L*, a*, b* system, L* represents the intensity of the color, a* indicates the green/red color axis and b* the blue/yellow color axis. The lower the value of L, the darker or more intense the color. The higher the value of a*, the redder the shade, and the higher the value of b*, the yellower the shade.

The variation in coloration between the dyed locks of natural/permanent-waved gray hair that are untreated (control) and after treatment are defined by ($\Delta E^*$) according to the following equation:

$$\Delta E^* = \sqrt{(L^*-L_o^*)^2 + (a^*-a_o^*)^2 + (b^*-b_o^*)^2}$$

In this equation, L*, a* and b* represent the values measured after dyeing permanent-waved hair containing 90% white hairs, and $L_o^*$, $a_o^*$ et $b_o^*$ represent the values measured for untreated permanent-waved hair containing 90% white hairs.

The higher the value of $\Delta E$, the greater the difference in color between the control locks and the dyed locks.

After rinsing, shampooing and drying the locks under a hood, the coloration of the hair is evaluated visually and read on a Minolta spectrocolorimeter (CM3600d, illuminant D65, angle 10°, SCI values) for the L*, a*, b* colorimetric measurements.

| | Examples (on permanent-waved natural hair containing 90% white hairs) | | |
|---|---|---|---|
| | Control (untreated hair) | 1 Comparative | 2 Invention |
| Composition A Step 1 | — | A1 | A2 |
| Composition B Step 2 | — | B1 | B2 |
| Shades on hair | — | Golden gray | Dark gray natural |

-continued

| | Examples (on permanent-waved natural hair containing 90% white hairs) | | |
|---|---|---|---|
| | Control (untreated hair) | 1 Comparative | 2 Invention |
| L* | 60.8 | 34.3 | 28.2 |
| a* | 1.1 | −0.7 | 0.2 |
| b* | 15.4 | 1.2 | −0.2 |
| ΔE | — | 30.1 | 36.2 |
| ΔL* | — | −26.5 | −32.6 |

It is seen from the results of the above table that the process according to the invention makes it possible to obtain significantly darker coloration (L and ΔL significantly lower) than that obtained via the comparative process.

In addition, the process according to the invention has greater dyeing power than that of the comparative process (significantly greater ΔE for the process of the invention).

The invention claimed is:

1. A process for dyeing keratin fibers, said process comprising the steps of:
A. applying to said keratin fibers:
composition (A) comprising:
i) at least one indole or indoline compound;
ii) at least one metal salt; and
iii) hydrogen peroxide or at least one system that generates hydrogen peroxide; and
B. applying to said keratin fibers:
a composition (B) comprising:
iv) at least one basifying agent.

2. The process according to claim 1, wherein the at least one indole or indoline compound is chosen from the compounds of formula (I) below:

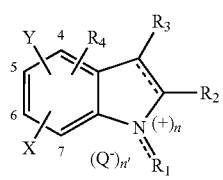

(I)

and organic or mineral acid or base salts thereof, optical isomers thereof, enantiomers and diastereoisomers, geometrical isomers and tautomers thereof, oligomers thereof, and solvates thereof;
wherein, in formula (I):
$R_1$ is chosen from a hydrogen atom, radical $(C_1-C_6)$alkyl groups, $(C_2-C_6)$alkenyl groups, $(C_1-C_6)$alkylcarbonyl groups, $(C_2-C_6)$alkenylcarbonyl groups, $(C_1-C_6)$alkylthiocarbonyl groups, $(C_2-C_6)$alkenylthiocarbonyl groups, and $R_g$—O—S(O)$_x$—,
wherein $R_g$ chosen from hydrogen atoms, alkali metals, alkaline-earth metals, and $(C_1-C_4)$alkyl groups, and x is 1 or 2,
said alkyl or alkenyl groups being optionally substituted, such as with a heterocyclic group optionally substituted with at least one carboxyl group;
$R_2$ is chosen from a hydrogen atom, radical $(C_1-C_6)$alkyl groups, and —C(Z)—Z'—$R_a$, wherein $R_a$ is chosen from a hydrogen atom, an alkali metal, an alkaline-earth metal, and radical $(C_1-C_6)$alkyl groups;
Z and Z', which may be identical or different, are chosen from oxygen and sulfur atoms, the groups $NR_b$ and $N^+R_bR_c$, and Q'$^-$; wherein Z' may also may also be chosen from a covalent a bond with $R_b$ and $R_c$;
$R_b$ and $R_c$, which may be identical or different, are chosen from hydrogen atoms and radical $(C_1-C_6)$ alkyl groups; and
Q' is chosen from anionic counterions;
$R_3$ is chosen from:
i) a hydrogen atom;
ii) radical $(C_1-C_6)$alkyl groups, optionally substituted especially with a group —$NR_bR_c$, —$N^+R_aR_bR_c$, Q'$^-$or —C(Z)—Z'—$R_a$, with Z, Z', $R_a$, $R_b$, $R_c$ and Q'$^-$ being as defined above; and
iii) a radical (II):

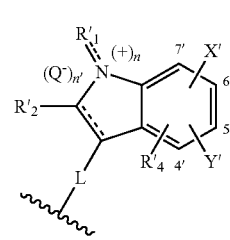

(II)

in which in radical (II):
L is chosen from covalent a bonds, divalent groups chosen from —Z— and —C(Z)Z'—, and divalent $(C_1-C_6)$alkylene groups, with Z and Z' as defined above;
$R'_1$, $R'_2$ and $R'_4$ are chosen from the same atoms or radicals as $R_1$, $R_2$ and $R_4$, as defined herein; and
∼∼ represents the point of attachment of the radical (II) to the rest of the molecule;
or alternatively $R_1$ and $R_2$ and/or $R_2$ and $R_3$ form, together with the atoms that bear them, a fused, optionally substituted heterocyclic group; or $R_2$ and $R_3$ form, together with the carbon atoms that bear them, a fused, optionally substituted aryl group;
$R_4$ is chosen from:
i) a hydrogen atom,
ii) a halogen atom
iii) a group —NRR',
iv) a group —OH,
v) radical $(C_1-C_6)$alkyl groups,
vi) radical $(C_1-C_6)$alkoxy groups,
vii) radical $(C_1-C_6)$alkylthio groups,
viii) aryloxy radical groups,
viii) arylthio radical groups,
ix) radical aryl$(C_1-C_6)$alkoxy groups,
x) radical aryl$(C_1-C_6)$alkylthio groups, and
xi) radical $R_aC(Z_a)$—$Z_b$— groups,
wherein $Z_a$ and $Z_b$ are chosen from oxygen and sulfur atoms, or $NR_b$,
where $R_a$ and $R_b$ are as defined herein; and xii) a radical (III):

(III)

in which in radical (III):
L is as defined herein;
$R'_1$, $R'_2$ and $R'_3$ are chosen from the same atoms or radicals as $R_1$, $R_2$ and $R_3$, as defined herein; and
~~~ represents the point of attachment of the radical (III) to the rest of the molecule;
X and X', which may be identical or different, are chosen from hydrogen atoms and radicals chosen from —NRR', —$OR_e$, —$SR_e$, ($C_1$-$C_6$)alkyl groups, and $R_aC(Z_a)$—$Z_b$—,
wherein $R_e$ is chosen from a hydrogen atom and ($C_1$-$C_6$) alkyl groups, aryl groups, and aryl($C_1$-$C_6$)alkyl groups;
Y and Y', which may be identical or different, are chosen from —$OR'_e$, —$SR'_e$, —NRR', $R_aC(Z_a)$—$Z_b$—, $R_f$—O—$S(O)_x$—$Z_d$—, and $R_f$—O—$S(O)_x$,
wherein $R_f$ is chosen from a hydrogen atom, alkali metals, alkaline-earth metals, and ($C_1$-$C_4$)alkyl groups, $Z_d$ is chosen from an oxygen atom and NR groups, wherein R is as defined herein, x is as defined herein, and $R'_e$ is chosen from the same atoms or radicals as $R_e$;
or alternatively the radicals $R_e$ and $R'_e$ of two contiguous groups X and X' and/or contiguous groups Y and Y' form, together with the oxygen or sulfur atom, a heterocyclic group;
the radicals X, Y, X' and Y' being located on any of the carbon atoms 4 to 7 and 4' to 7', respectively;
R and R', which may be identical or different, represent a hydrogen atom or an optionally substituted group ($C_1$-$C_6$)alkyl;
‒‒‒ represents a single bond or a double bond;
n is 0 when the bond between $R_1$ and N or R', and N is a single bond;
n is 1 when the group $R_1$ or R', represents an alkenyl group and when the end connected to the nitrogen atom is a double bond;
$Q^-$ is chosen from anionic counterions; and
n' is 0 or 1;
with the proviso that:
$R_3$ cannot represent the radical (II) when $R_4$ represents a radical (III); and
when n is 0, then n' is 0, when n is 1, then n' is 1, or n' is 0, in which case a radical —C(Z)—Z'—$R_a$ is in the anionic form —C(Z)—$Z'^-$.

3. The process according to claim 2, wherein the compounds of formula (I) are monomers and $R_3$ is chosen from i) a hydrogen atom and ii) an optionally substituted radical ($C_1$-$C_6$)alkyl group.

4. The process according to claim 2, wherein the compounds of formula (I) are dimmers and $R_3$ is chosen from a radical (II) or $R_4$ represents a radical (III).

5. The process according to claim 2, wherein the compounds of formula (I) are indole compounds, with the bond ‒‒‒ between the carbon atoms bearing the radicals $R_2$ and $R_3$ representing a double bond.

6. The process according to claim 2, wherein the compounds of formula (I) are indole compounds of formula (Ia) below:

(Ia)

in which in formula (Ia):
$R_1$ and $R_3$, which may be identical or different, are chosen from a hydrogen atom and $C_1$-$C_4$ alkyl groups;
$R_2$ is chosen from a hydrogen atom, $C_1$-$C_4$ alkyl groups, and —COOH groups;
X is chosen from a hydrogen atom, —$NH_2$, —OH, $C_1$-$C_4$ alkyl groups, $C_1$-$C_4$ alkoxy groups, and —O—C(O)—R groups, wherein R is chosen from H and $C_1$-$C_4$ alkyl groups; and
Y is chosen from —OH, —$NH_2$, and —O—C(O)—R groups, wherein R is chosen from H and $C_1$-$C_4$ alkyl groups;
and salts thereof.

7. The process according to claim 2, wherein the compounds of formula (I) are chosen from:

(1)

5,6-dihydroxyindole (2)

2-methyl-5,6-dihydroxyindole (3)

3-methyl-5,6-dihydroxyindole (4)

4-hydroxyindole

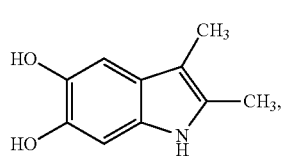

2,3-dimethyl-5,6-dihydroxyindole

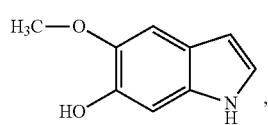

6-hydroxy-5-methoxyindole

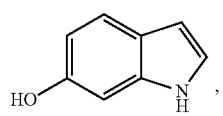

6-hydroxyindole

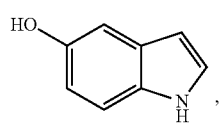

5-hydroxyindole

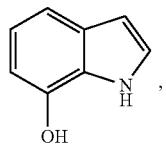

7-hydroxyindole

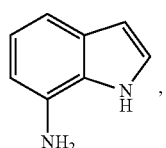

7-aminoindole

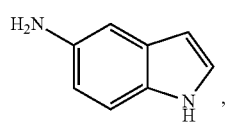

5-aminoindole

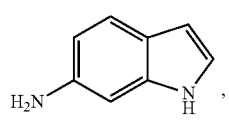

6-aminoindole

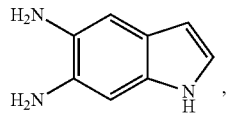

5,6-diaminoindole

4-aminoindole

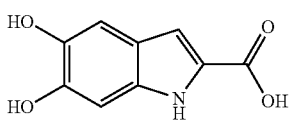

5,6-dihydroxyindole-2-carboxylic acid, or 5,6-dihydroxy-1H-indole-2-carboxylic acid

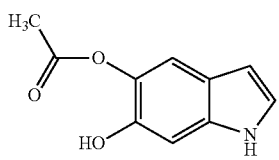

5-acetyloxy-6-hydroxyindole

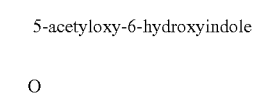

5,6-dimethylcarbonyloxy-1-methyl-1H-indole

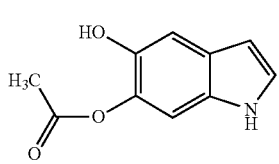

6-acetyloxy-5-hydroxyindole

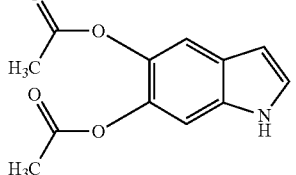

5,6-diacetyloxyindole

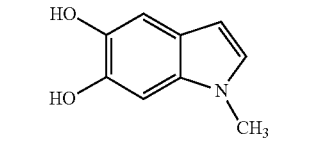

5,6-dihydroxy-1-methyl-1H-indole or 1-methyl-5,6-dihydroxyindole

(21)
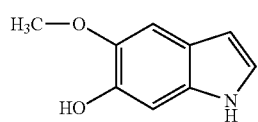
6-hydroxy-5-methoxyindole

(22)
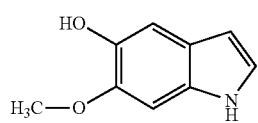
5-hydroxy-6-methoxyindole

(23)
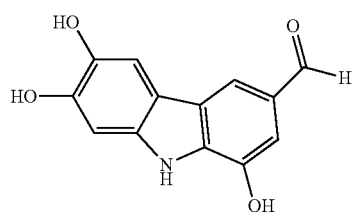
1,6,7-trihydroxy-9H-carbazole-3-carboxaldehyde

(24)
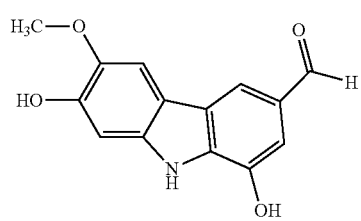
1,7-dihydroxy-6-methoxy-9H-carbazole-3-carboxaldehyde

(25)
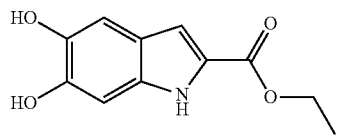
ethyl 5,6-dihydroxy-1H-indole-2-ylcarboxylate

(26)
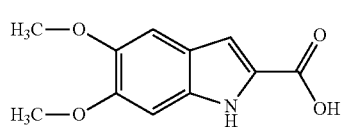
5,6-dimethoxy-1H-indole-2-carboxylic acid

(27)
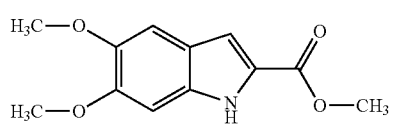
methyl 5,6-dimethoxy-1H-indole-2-ylcarboxylate

(28)
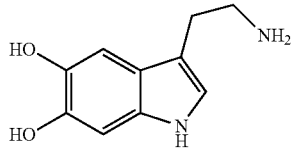
5,6-dihydroxytryptamine

(29)
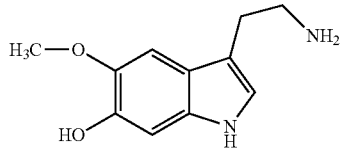
6-hydroxy-5-methoxytryptamine

(30)
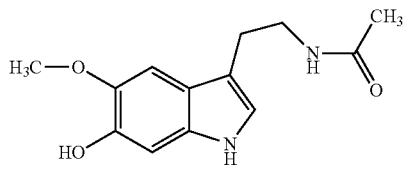
6-hydroxymelatonin

(31)
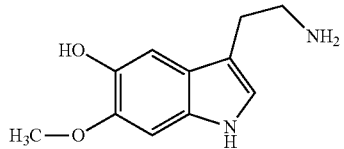
5-hydroxy-6-methoxytryptamine

(32)
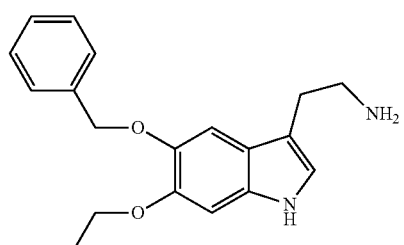
5,6-dibenzoxytryptamine

(33)
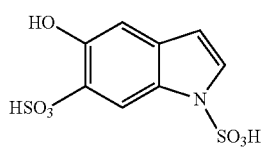
Ancorinolate B (34)

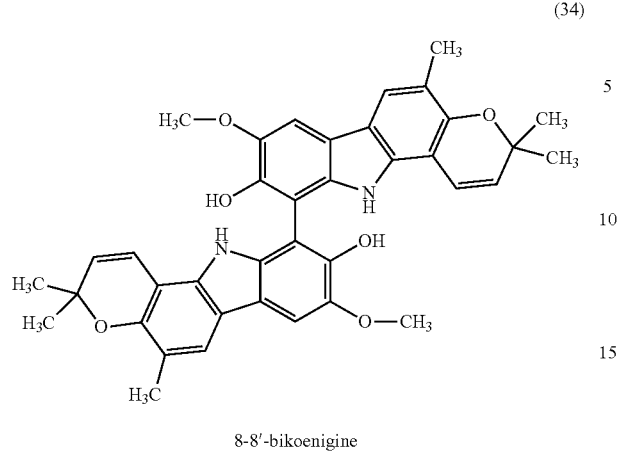

8-8'-bikoenigine (35)

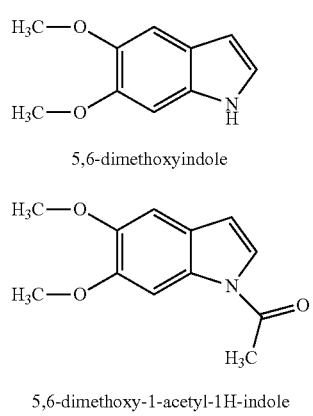

5,6-dimethoxyindole (36)

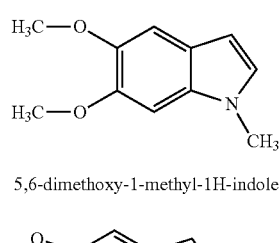

5,6-dimethoxy-1-acetyl-1H-indole (37)

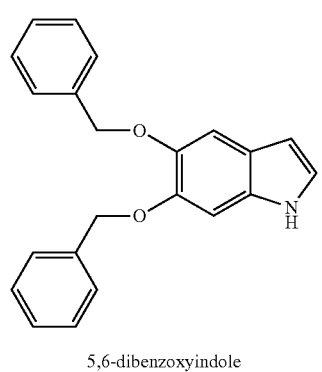

5,6-dimethoxy-1-methyl-1H-indole (38)

5,6-methylenedioxyindole (39)

5,6-dibenzoxyindole (40)

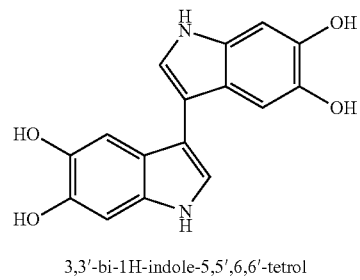

3,3'-bi-1H-indole-5,5',6,6'-tetrol (41)

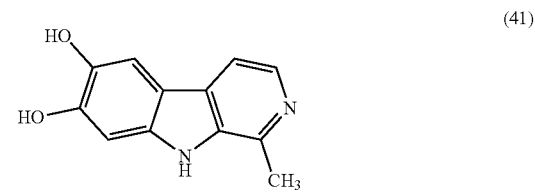

6,7-dihydroxy-1-methyl- -carboline or 1-methyl-9H-pyrido[3,4-b]indole-6,7-diol (42)

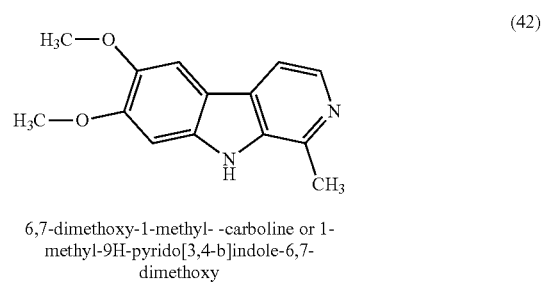

6,7-dimethoxy-1-methyl- -carboline or 1-methyl-9H-pyrido[3,4-b]indole-6,7-dimethoxy (43)

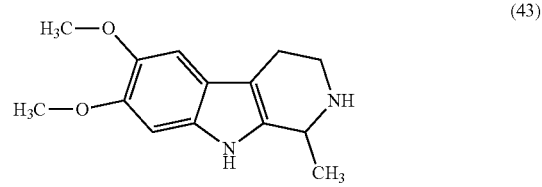

1,2,3,4-tetrahydro-6,7-dimethoxy-1-methyl- -carboline (44)

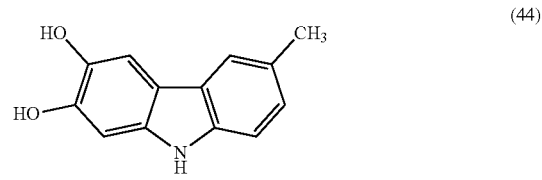

2,3-dihydroxy-6-methyl-9H-carbazole (45)

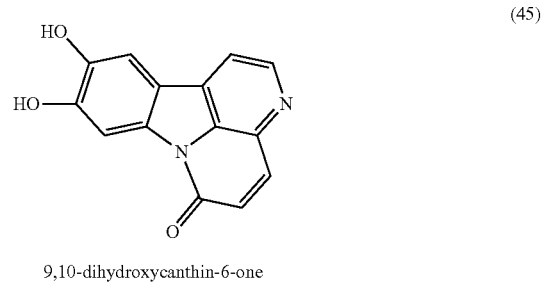

9,10-dihydroxycanthin-6-one

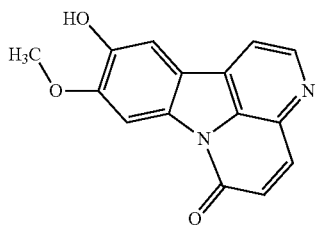

10-hydroxy-9-methoxycanthin-6-one

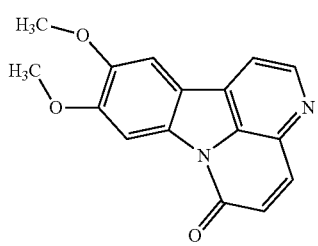

9,10-dimethoxycanthin-6-one

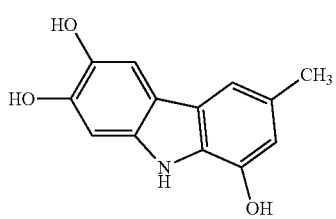

1,6,7-trihydroxy-3-methylcarbazole

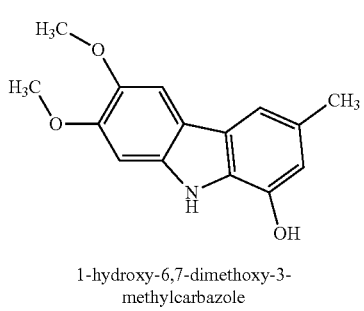

1-hydroxy-6,7-dimethoxy-3-methylcarbazole

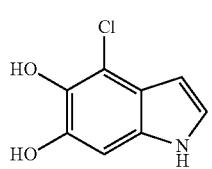

4-chloro-5,6-dihydroxyindole (46)

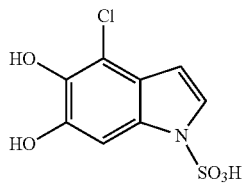

4-chloro-5,6-dihydroxy-1H-indole-1-sulfonic acid (47)

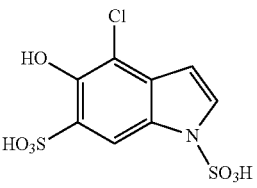

4-chloro-5-hydroxy-1H-indole-1,6-disulfonic acid and organic or mineral acid or base salts thereof.

8. The process according to claim 2, wherein the compounds of formula (I) are indole compounds, with the bond ---- between the carbon atoms bearing the radicals $R_2$ and $R_3$ representing a single bond.

9. The process according to claim 2, wherein the compounds of formula (I) are indoline compounds of formula (Ib) below:

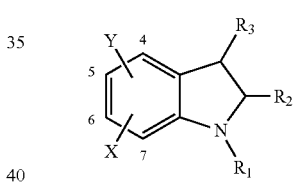

in which in formula (Ib),
$R_1$, $R_2$, $R_3$, X, and Y have the same meanings as for the compounds of formula (Ia), and enantiomers, diastereoisomers and salts thereof.

10. The process according to claim 2, wherein the compounds of formula (I) are indoline compounds chosen from 5,6-dihydroxyindoline, N-methyl-5,6-dihydroxyindoline, N-ethyl-5,6-dihydroxyindoline, N-butyl-5,6-dihydroxyindoline, 4-hydroxy-5-methoxyindoline, 6-hydroxy-7-methoxyindoline, 6,7-dihydroxyindoline, 4,5-dihydroxyindoline, 5-methoxy-6-hydroxyindoline, compounds of formula (IV), and the decarboxylated forms thereof, of formula (IV'):

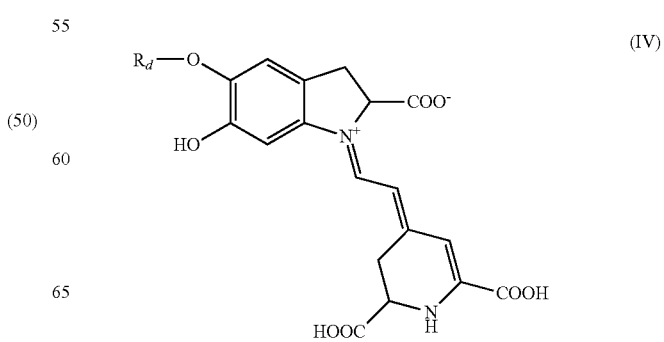

-continued

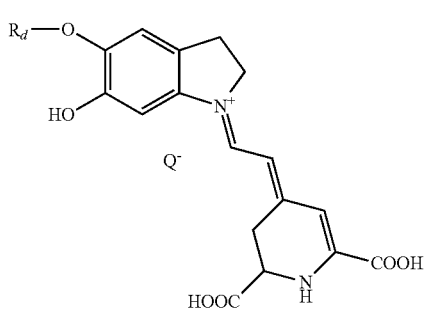

(IV')

in which formulae (IV) and (IV')
$R_d$ is chosen from a hydrogen atom, glucosyl radicals, and 6'-O-malonylglucosyl radicals, and $Q^-$ is chosen from anionic counterions, with the proviso that $Q^-$ is absent if one of the carboxyl groups is in anionic form —COO$^-$;
and enantiomers, diastereoisomers, and tautomers thereof, and organic and mineral acid or base salts thereof.

11. The process according to claim 2, wherein at least one of the following conditions are satisfied:
$R_1$ is chosen from radical $(C_1$-$C_4)$alkyl groups and the following group:

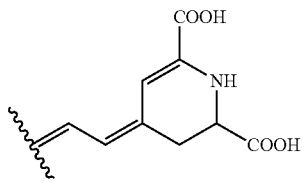

wherein n is 1 and ~~~ represents the point of attachment of the radical to the ammonium $N^+$ of the compound of formula (I);
$R_3$ is chosen from radical $(C_1$-$C_4)$alkyl groups;
in radical (II), L is chosen from a σ bond;
$R_4$ is chosen from hydrogen, chlorine, —NH$_2$, and benzoxy;
at least one of X, X', Y, and Y' are chosen from —NH$_2$, a hydroxyl group, or $R_a$—C(O)—O— groups; and
X and Y are in position 5 and 6; X' and Y' are in position 5' and 6'.

12. The process according to claim 1, wherein the at least one indole or indoline compound is chosen from animal, bacterial, fungal, algal, and plant extracts.

13. The process according to claim 1, further comprising at least one additional natural ortho-diphenol.

14. The process according to claim 13, wherein the at least one additional natural ortho-diphenol is chosen from:
extracts of tea leaves, extracts of rosemary leaves, and extracts of mate leaves;
extracts of fruit and extracts of cocoa beans or pods;
extracts of legumes;
extracts of tree wood;
extracts of quebracho wood;
extracts of braziletto wood; and
extracts of gall nuts.

15. The process according to claim 1, wherein the at least one metal salt ii) is chosen from Mn and Zn salts.

16. The process according to claim 15, wherein the Mn and Zn salts are chosen from the halides, sulfates, phosphates, nitrates, perchlorates, carboxylic acid salts, and mixtures thereof.

17. The process according to claim 1, wherein the composition comprises, as component iii), hydrogen peroxide or urea peroxide.

18. The process according to claim 1, wherein the composition comprises, as component iii), at least one of:
polymer complexes that can release hydrogen peroxide, chosen from polyvinylpyrrolidone/$H_2O_2$;
oxidases that produce hydrogen peroxide in the presence of a suitable substrate;
perborates; and
percarbonates.

19. The process according to claim 1, wherein the at least one basifying agent is chosen from mineral and organic basifying agents.

20. The process according to claim 19, wherein the at least one basifying agent is chosen from alkali metal and alkaline-earth metal (bi)carbonates.

21. The process according to claim 1, further comprising at least one post-treatment step chosen from shampooing with a standard shampoo, rinsing, and drying keratin fibers by heat treatment; with the proviso that said process does not involve intermediate rinsing immediately before step (B) comprising applying composition (B).

22. The process according to claim 1, further comprising an additional step just before step (B) comprising applying composition (B) comprising component iv), wherein the keratin fibers are:
a) mechanically wiped, or
b) dried by heat with a heat treatment.

23. A multi-compartment device comprising from 2 to 4 compartments, containing from 2 to 4 compositions, in which are distributed a composition comprising components i), ii), iii) and iv), wherein the composition comprises:
i) at least one indole or indoline compound;
ii) at least one metal salt; and
iii) hydrogen peroxide or at least one system that generates hydrogen peroxide; and
iv) at least one basifying agent.

* * * * *

UNITED STATES PATENT AND TRADEMARK OFFICE
CERTIFICATE OF CORRECTION

PATENT NO. : 8,597,373 B2
APPLICATION NO. : 13/701827
DATED : December 3, 2013
INVENTOR(S) : Frédéric Guerin et al.

Page 1 of 1

It is certified that error appears in the above-identified patent and that said Letters Patent is hereby corrected as shown below:

In the Claims

Claim 2, column 30, line 35, please change "covalent a bonds," to -- covalent σ bonds, --.

Claim 2, column 31, line 29, please change "S(O)x," (second occurrence) to -- S(O)x–, --.

Signed and Sealed this
Eighteenth Day of March, 2014

Michelle K. Lee
*Deputy Director of the United States Patent and Trademark Office*